(12) United States Patent
Kim

(10) Patent No.: US 8,877,889 B2
(45) Date of Patent: Nov. 4, 2014

(54) TUMOR CELL-KILLING PEPTIDES

(75) Inventor: Tae-Hyoung Kim, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 127 days.

(21) Appl. No.: 13/393,394

(22) PCT Filed: Aug. 16, 2010

(86) PCT No.: PCT/KR2010/005391
§ 371 (c)(1),
(2), (4) Date: Mar. 5, 2012

(87) PCT Pub. No.: WO2011/027980
PCT Pub. Date: Mar. 10, 2011

(65) Prior Publication Data
US 2012/0165269 A1    Jun. 28, 2012

Related U.S. Application Data

(60) Provisional application No. 61/239,423, filed on Sep. 2, 2009.

(51) Int. Cl.
*C07K 7/00* (2006.01)
*C07K 14/47* (2006.01)
*A61K 38/00* (2006.01)

(52) U.S. Cl.
CPC .............. *C07K 14/4747* (2013.01); *A61K 38/00* (2013.01)
USPC ........................... 530/325; 530/326; 514/19.3

(58) Field of Classification Search
None
See application file for complete search history.

(56) References Cited

U.S. PATENT DOCUMENTS

2006/0019922 A1   1/2006   Juliano et al.
2009/0130712 A1 * 5/2009   McKenna et al. ............ 435/69.1

FOREIGN PATENT DOCUMENTS

| WO | 03/040693 | * | 5/2003 |
| WO | 03/093478 | * | 11/2003 |
| WO | 2006/001582 | * | 1/2006 |
| WO | WO 2011/027980 A3 | | 3/2011 |

OTHER PUBLICATIONS

Seo et al., "The Molecular Mechanism of Noxa-Induced Mitochondrial Dysfunction in p53-Mediated Cell Death," J. Biol. Chem. 278:48292-48299, 2003.

* cited by examiner

*Primary Examiner* — Sheela J Huff
(74) *Attorney, Agent, or Firm* — Clark & Elbing LLP

(57) ABSTRACT

The present invention provides a tumor cell-killing peptide and a pharmaceutical composition for treating a cancer. The tumor cell-killing peptide of the present invention selectively homes into tumor cells so that it can induce the death of tumor cells effectively while minimizing the harming of normal cell.

8 Claims, 23 Drawing Sheets

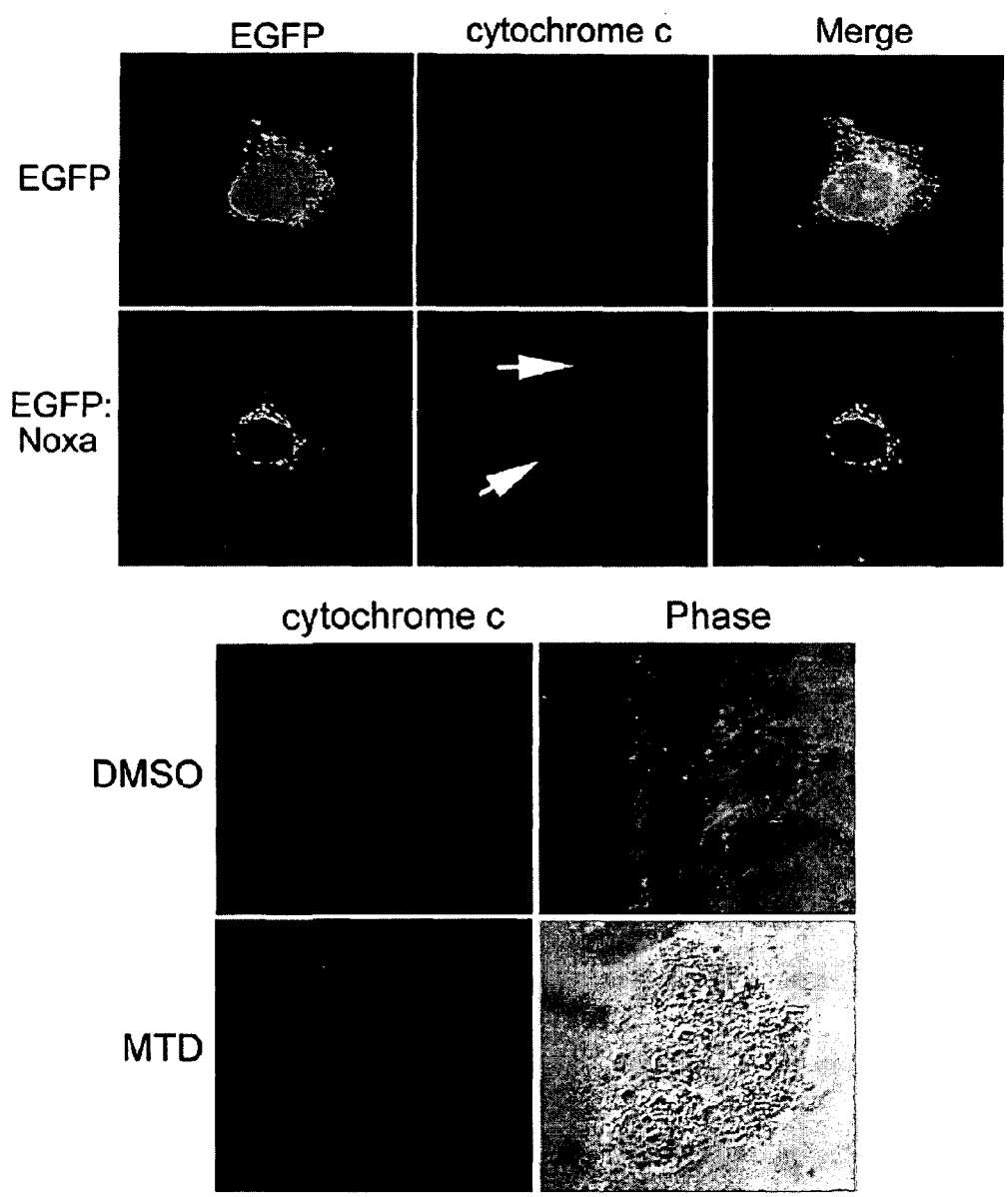

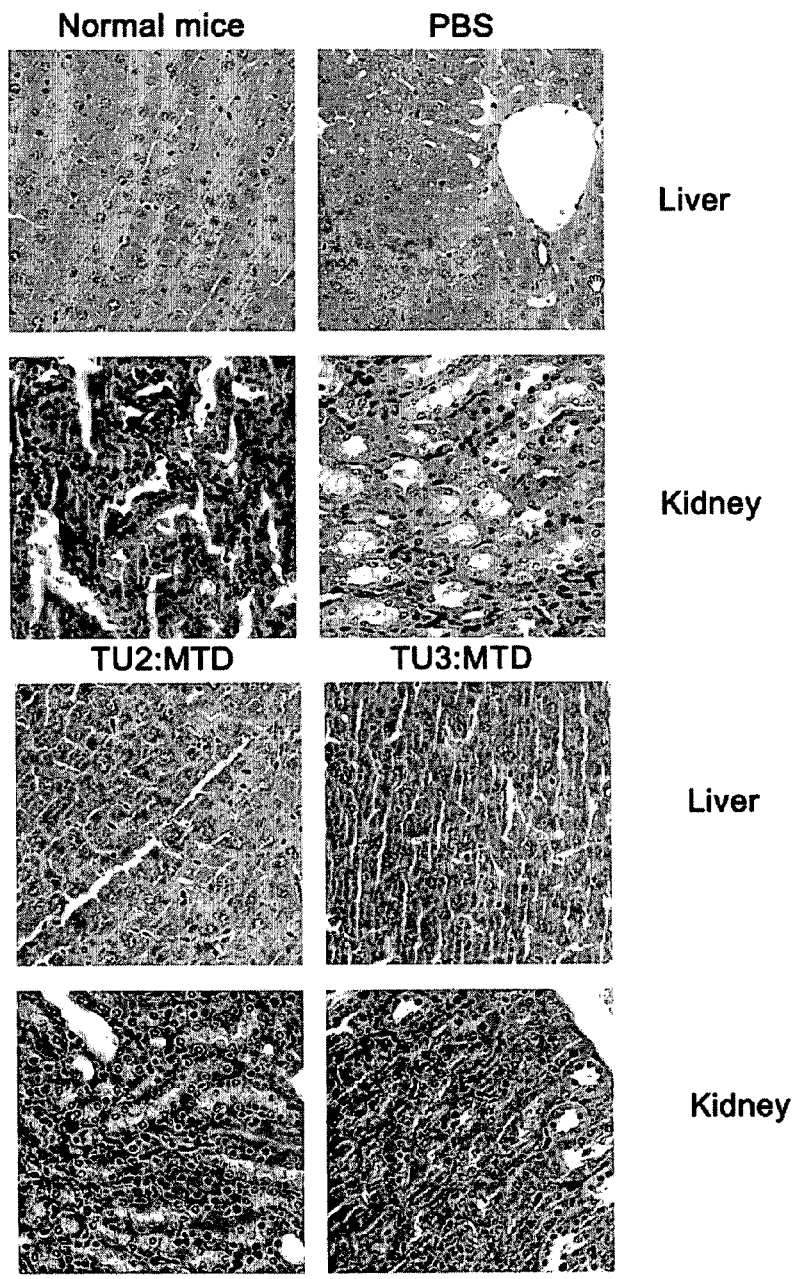

TUMOR CELL-KILLING PEPTIDES

CROSS-REFERENCE TO RELATED APPLICATIONS

This application is the U.S. national stage filing under 35 U.S.C. §371 of international application PCT/KR2010/005391, filed Aug. 16, 2010, which claims benefit of U.S. Provisional Patent Application 61/239,423, filed Sep. 2, 2009.

CROSS-REFERENCE TO RELATED APPLICATIONS

This application claims priority from U.S. Pat. Appln. No. 61/239,423 filed on Sep. 2, 2009 in the USPTO, the disclosure of which is incorporated herein by reference.

STATEMENT AS TO GOVERMENT-FUNDED RESEARCH

This invention was made with Korean Government support under a grant (No. R13-2003-009-01002-0) funded by the Korea Science and Engineering Foundation (to T-H Kim), a grant (R01-2006-000-10451-0) from the Basic Research Program of the Korea Science & Engineering Foundation (to T-H Kim), and a grant (to Y-W, Seo) from the Establishment of Joint-Use Equipments for Degenerative Diseases Research (Korea Basic Science Institute) awarded by the Ministry of Science & Technology.

BACKGROUND OF THE INVENTION

1. Field of the Invention

The present invention relates to a tumor cell-killing peptide and a pharmaceutical composition for treating a cancer comprising the tumor cell-killing peptide.

2. Description of the Related Art

Apoptosis is a fine-tuned mechanism to eliminate harmful, seriously damaged, or unnecessary cells in multi-cellular organisms. Apoptosis plays an important role to grow a normal cell, to maintain cell homeostasis, to prevent cancer and other diseases, and to protect a living body from viral or bacterial infection. Extensive lines of evidence indicate that the mitochondria act as regulators of apoptosis, and mitochondrial integrity is controlled by the Bcl-2 family proteins (1). Bcl-2 family members are divided into two main groups according to whether they promote or inhibit apoptosis. The anti-apoptotic members (e.g., Bcl-2 and Bcl-$_{XL}$) possess four BH domains from BH1 to BH4, whereas the pro-apoptotic members (e.g., Bax and Bak) have three BH domains from BH1 to BH3. The BH3-only proteins (e.g., Bid, Noxa and PUMA) induce apoptosis by activating pro-apoptotic proteins like Bax and Bak or inhibiting anti-apoptotic proteins like Bcl-2 and Mcl-1 (2, 3).

Mouse Noxa, originally identified as a p53 target gene, plays a crucial role in apoptosis iduced by p53-dependent genotoxic stimuli (4-7). Two functional domains in Noxa, the BH3 domain and the mitochondrial targeting domain (MTD), have been identified (8). Recent studies indicate that the Noxa BH3 domain is crucial to the protein's ability to induce cell death by the selective inhibition of Mcl-1 and A1/Bfl-1 (1, 9-13). On the other hand, deletion of the Noxa MTD completely abolished cell death in HeLa cells mainly due to the loss of Noxa mitochondrial localization (8). Thus, it was thought that the MTD of Noxa delivers the BH3 domain of Noxa to the mitochondria, where the BH3 domain binds to Mcl-1 and A1/Bfl-1 resulting in inactivation of anti-apoptotic activities of Mcl-1 and A1/Bfl-1. This hypothesis suggests that cell death-inducing activity of Noxa solely depends on the capability of Noxa BH3 domain to inactivate Mcl-1 and A1/Bfl-1 function. However, Noxa mutant carrying mutation in BH3 domain cannot completely abolish the cell death-inducing activity of Noxa (6, 14), indicating that there is another potential killing domain in Noxa.

DETAILED DESCRIPTION OF THIS INVENTION

The present inventors have made intensive researches to develop a peptide drug which can induce the death of tumor cells safely and effectively. As results, we have discovered that a combination of a mitochondria targeting domain of Noxa protein and a specific tumor homing motif can selectively target to the tumor regions and induce massive cell death of tumor cells but not normal cells.

Accordingly, it is an object of this invention to provide a tumor cell-killing peptide.

It is another object of this invention to provide a pharmaceutical composition for treating a cancer comprising the tumor cell-killing peptide.

Other objects and advantages of the present invention will become apparent from the following detailed description together with the appended claims and drawings.

In one aspect of this invention, there is provided a tumor cell-killing peptide, comprising (a) a mitochondria targeting domain (MTD) comprising the amino acid sequence of SEQ ID NO:1 or its homologous sequence having at least 70% homology to the amino acid sequence of SEQ ID NO:1; and (b) a tumor homing motif comprising the amino acid sequence of SEQ ID NO:2 or SEQ ID NO:3.

The present inventors have made intensive researches to develop a peptide drug which can induce the death of tumor cells safely and effectively. As results, we have discovered that a combination of a mitochondria targeting domain of Noxa protein and a specific tumor homing motif can selectively target to the tumor regions and induce massive cell death of tumor cells but not normal cells.

The present invention comprises MTD, which is a mitochondria targeting domain of Noxa protein and has a pro-death activity.

Noxa protein, one of the "BH3-only" members of Bcl-2 family, can stimulate apoptosis by regulating mitochondria function. BH3 domain of Noxa protein plays a crucial role in inducing an apoptosis and MTD domain of Noxa without BH3 was known not to have a cell killing activity. However, the present inventors have found that a mitochondria targeting domain (MTD) at the C-terminus of Noxa protein can also induce the cell death without BH3 domain when combined with a specific tumor homing motif.

The MTD used in the present invention comprises the amino acid sequence set forth in SEQ ID NO:1 (KLLN-LISKLF), which is a mitochondria targeting domain of human Noxa protein.

Alternatively, the MTD used in the present invention comprises a homologous sequence of SEQ ID NO:1 having at least 70% homology to the SEQ ID NO:1.

The sequence homology of peptides may be decided by comparing the natural sequence and a variant sequence using the conventional computer programs. For example, GAP computer program version 6.0 (Devereux et al., Nucl. Acids Res., 12:387(1984)) which is commercially available from University of Wisconsin Genetics Computer Group (UWGCG) can be used. Homology searches also can be easily done over using the program BLAST (Basic Local Alignment Search Tool) from NCBI (National Center for Biotechnology Information, Washington, D.C.).

According to a preferable embodiment, the homologous sequence of SEQ ID NO:1 having at least 70% homology comprises leucines at the 5$^{th}$ and 9$^{th}$ positions. The homologous sequence may be prepared by substituting 1 to 3 amino acids of SEQ ID NO:1 to have at least 70% homology; however it is advisable to conserve the 5$^{th}$ and 9$^{th}$ leucines of SEQ ID NO:1 because the two leucines play an important role in inducing cell death.

Examples of the homologous sequence of SEQ ID NO:1 having at least 70% homology may include, but not limited to, the amino acid sequence of SEQ ID NO 4 (KALNLISKLF), the amino acid sequence of SEQ ID NO 5 (KLAALISKLF), the amino acid sequence of SEQ ID NO 6 (KLLNLIAALF), and the amino acid sequence of SEQ ID NO 7 (KALNLIAALF).

According to another preferable embodiment, the tumor cell-killing peptide comprising the MTD of the present invention causes massive necrosis through an abrupt increase of cytosolic calcium released from the mitochondria by opening the mitochondrial permeability transition (mPT) pore.

The tumor cell-killing peptide of the present invention also comprises a tumor homing motif to selectively target tumor cell regions.

If the MTD domain used in the present invention is combined just with a protein transduction domain (PTD) such as R8, it acts on both normal and tumor cells (or tissues). As such, one of the challenges in treating tumors is maximizing the killing of tumor cells while minimizing the harming of healthy tissue. The present inventors found that the specific tumor homing motif used in the present invention can transfer the MTD, the pro-death domain, to the tumor region selectively and has no harm to normal cells.

In addition, it is crucial that the MTD domain enters into tumor cells for their tumor-cell killing effects. The specific tumor homing motif used in the present invention also permits the MTD domain as a pro-death domain to be introduced into tumor cells.

According to a preferable embodiment, the tumor homing motif, which enables the MTD domain to be targeted to and delivered into tumor cells, comprises the amino acid sequence set forth in SEQ ID NO:2.

In another preferable embodiment, the tumor homing motif of the present invention comprises the amino acid sequence set forth in SEQ ID NO:3.

The term "tumor" means a mass of cells that are characterized, at least in part, by containing angiogenic vasculature. A tumor may be benign, pre-malignant or malignant. Malignant tumor refers to cancer.

The term "cancer" refers to human and animal cancers and carcinomas, sarcomas, adenocarcinomas, lymphomas, leukemias, solid and lymphoid cancers, etc. Examples of different types of cancer include, but are not limited to, colon cancer, cervical cancer, prostate cancer, renal cancer (i.e., renal cell carcinoma), bladder cancer, lung cancer, breast cancer, thyroid cancer, liver cancer (i.e., hepatocarcinoma), pleural cancer, pancreatic cancer, ovarian cancer, uterine cancer, cervical cancer, testicular cancer, anal cancer, pancreatic cancer, bile duct cancer, gastrointestinal carcinoid tumors, esophageal cancer, gall bladder cancer, rectal cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, small cell lymphoma, large cell lymphoma, monocytic leukemia, myelogenous leukemia, acute lymphocytic leukemia, acute myelocytic leukemia, and multiple myeloma.

According to a preferable embodiment, the tumor cell-killing peptide of the present invention has a killing activity to colon tumor cells, lung tumor cells or cervical tumor cells, more preferably to colon tumor cells.

In an exemplary embodiment, the tumor homing motif and the MTD of the present invention may be directly fused or joined by linkers, spacers, or adapters. The number of amino acids comprising the linker can be determined by routine experimentation by a skilled artisan. The linkers may comprise a sufficient number of amino acids such that the MTP and the tumor homing motif function without interference from each other. Accordingly, amino acids that comprise the linker preferably do not substantially alter biological activity of the MTP and the tumor homing motif.

In a preferable embodiment, a peptide linker is used to join the tumor homing motif and the MTD of the present invention. For example, the peptide linker includes but not limited to glycine polymers $(G)_n$, glycine-serine polymers (including, for example, $(GS)_n$, $(GSGGS)_n$ and $(GGGS)_n$, where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are preferred since both of these amino acids are relatively unstructured, and therefore may be able to serve as a neutral tether between components. Glycine polymers are the most preferred as glycine accesses significantly more phi-psi space than even alanine, and is much less restricted than residues with longer side chains (see Scheraga, Rev. Computational Chem. III73-142 (1992), expressly incorporated by reference). Secondly, serine is hydrophilic and therefore able to solubilize what could be a globular glycine chain. Third, similar chains have been shown to be effective in joining subunits of recombinant proteins such as single chain antibodies.

More preferably, the peptide linker used to join the tumor homing motif and the MTD of the present invention may be a glycine oligomer, most preferably a $(Gly)_{2-3}$.

According to another preferable embodiment, the tumor cell-killing peptide of the present invention comprises the tumor homing motif at its N-terminal region and the MTD at its C-terminal region and the MTD and the tumor homing motif are linked by a peptide linker.

The tumor cell-killing peptide of the present invention may be prepared in accordance with a variety of methods. For example, it may be produced by gene cloning methods or solid-phase synthesis techniques. More specifically, the nucleotide sequences coding for the tumor cell-killing peptide are transformed into suitable host cells and expressed to produce tumor cell-killing peptides (see Sambrook, J. et al., *Molecular Cloning. A Laboratory Manual,* 3rd ed. Cold Spring Harbor Press(2001)). In some embodiments, the nucleotide sequences optionally encode linkers, crosslinkers, spacers, or adapters, as needed. Alternatively, the tumor cell-killing peptide of the present invention may be produced in accordance with solid-phase synthesis techniques known to one of skill in the art (Merrifield, *J. Amer. Chem. Soc.* 85:2149-54(1963); Stewart, et al., *Solid Phase Peptide Synthesis,* 2nd. ed., Pierce Chem. Co.: Rockford, 111(1984)).

The tumor cell-killing peptide of the present invention may be modified for much higher stability, inter alfa, serum stability. Preferably, the peptides of this invention have at their N-terminal or C-terminal a protection group selected from the group consisting of acetyl group, fluorenyl methoxy carbonyl group, formyl group, palmitoyl group, myristyl group, stearyl group or polyethylene glycol (PEG).

As demonstrated in Examples, the tumor-cell killing peptide of this invention can be highlighted as druggable peptide molecules for cancer therapy. The tumor-cell killing peptide is capable of specifically homing to tumor cells and selectively killing tumor cells.

In another aspect of this invention, there is provided a pharmaceutical composition for treating a cancer, comprising the tumor cell-killing peptide of the present invention as an active ingredient.

In still another aspect of this invention, there is provided a method for treating a cancer, which comprises administering to a subject in need thereof a composition comprising the tumor cell-killing peptide of the present invention as an active ingredient.

The term "active ingredient" refers to a therapeutically active compound, as well as any prodrugs thereof and pharmaceutically acceptable salts, hydrates and solvates of the compound and the prodrugs.

The pharmaceutical composition of the present invention is effective in treatment of cancers. Exemplified cancers treated by the pharmaceutical composition include stomach cancer, lung cancer, breast cancer, ovarian cancer, liver cancer, bronchogenic cancer, nasopharyngeal cancer, laryngeal cancer, pancreatic cancer, bladder cancer, colon cancer, cervical cancer, brain cancer, prostate cancer, bone cancer, skin cancer, thyroid cancer, parathyroid cancer and ureter cancer, but not limited to. Preferably, the cancers treated by the pharmaceutical composition may be colon cancer and cervical cancer, and more preferably colon cancer.

The pharmaceutical composition of the present invention may further comprise a pharmaceutically acceptable carrier.

The phrase "pharmaceutically acceptable" indicates that the substance or composition must be compatible chemically and/or toxicologically, with the other ingredients comprising a formulation, and/or the mammal being treated therewith. The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

The pharmaceutical composition of this invention may be administered orally or parenterally. For non-oral administration, intravenous injection, subcutaneous injection, intramuscular injection, intraperitoneal injection, transdermal administration or intratumoral injection may be employed.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Preferably, the pharmaceutical composition of the present invention is administered with a daily dose of from 0.001 µg/kg to 1000 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

(A) Schematic diagram of peptides used in experiments.

(B) HeLa cells were treated with DMSO or the indicated peptides in increasing doses (10 µM, 20 µM, and 30 µM). % of cell death was determined at 10 minutes after treatment by counting the dead cells and survived cells under the light microscope.

(C) Schematic diagrams of Noxa deletion mutants.

(D) HeLa cells were transfected with deletion mutants of Noxa. At 11 hrs, 24 hrs, and 36 hrs after transfection, cell death was determined by counting EGFP-positive dead cells with morphological changes using the fluorescent microscope.

(E) HeLa cells were transfected with substitution mutants of MTD peptide. These variants of MTD also showed the cell-killing activities (MTD—SEQ ID NO:1, MTD2—SEQ ID NO:4, MTD3—SEQ ID NO:5, MTD 4—SEQ ID NO:6 and MTD5—SEQ ID NO:7).

Figure 2A:
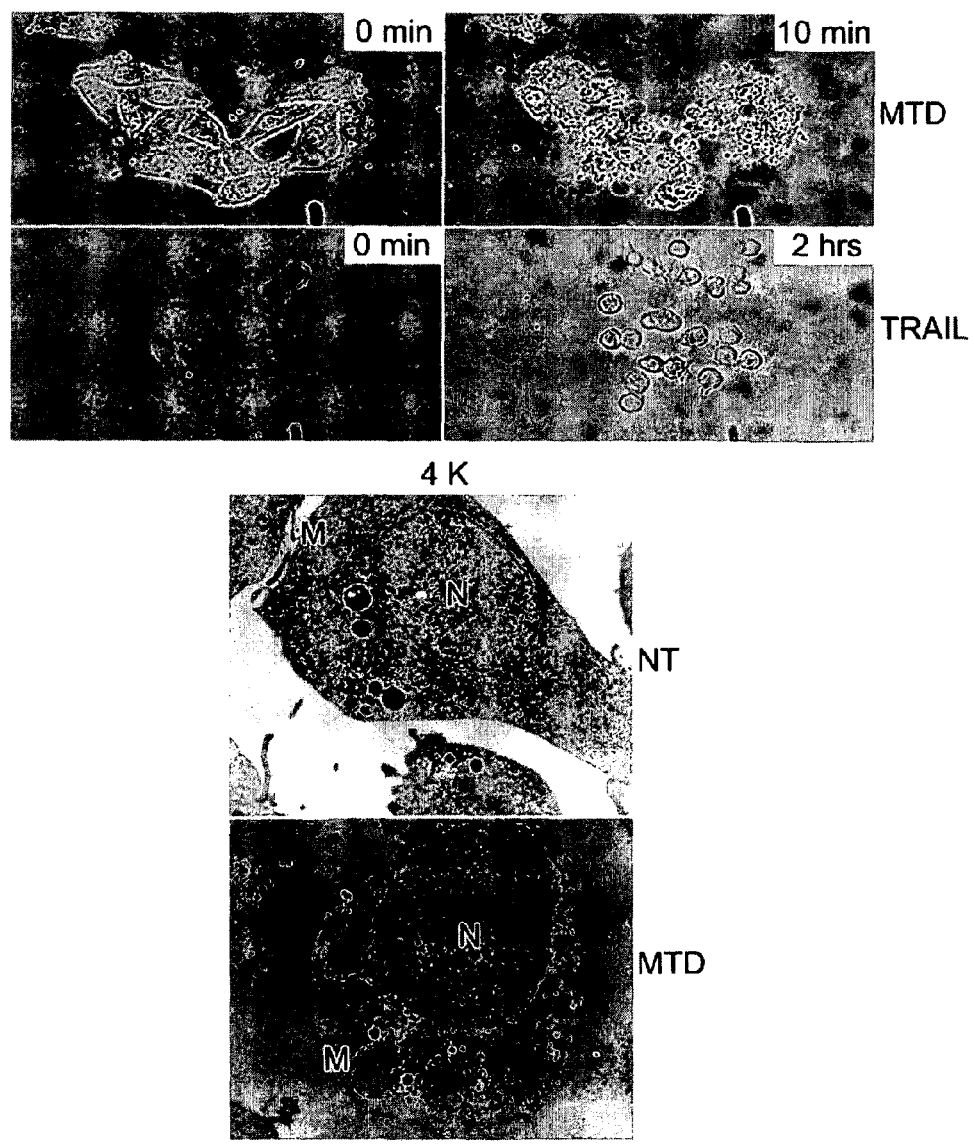
Figure 2C:
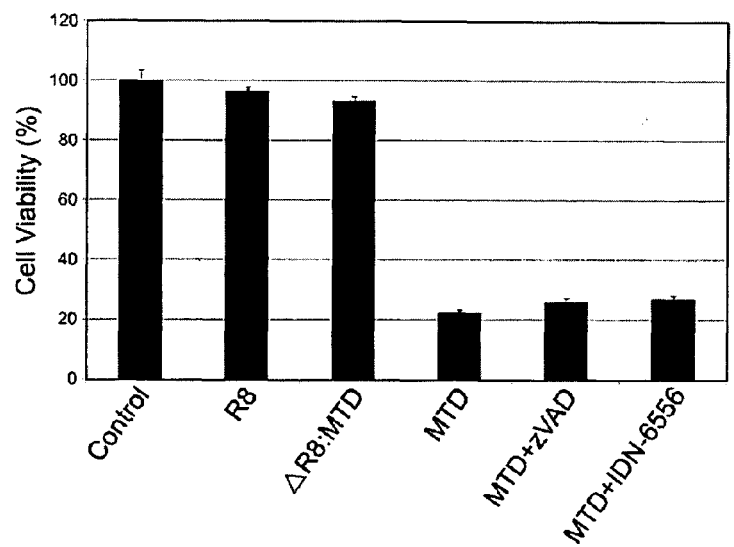

FIG. 2A-2C. Characteristics of MTD peptide-induced cell death.

(A) HeLa cells were treated with MTD peptides (10 µM), or TRAIL (100 ng/ml). Images were taken at the indicated times (upper panel). Jurkat cells were treated with MTD peptide (10 µM) for 10 minutes, cells were processed for TEM. Images were obtained with 4,000× magnification (lower panel). N: nucleus, M: mitochondrion.

(B) Plasmids (control vector or Noxa WT fused to GFP) were transfected into HeLa cells. After 2 days in the presence of zVAD-fmk, cytochrome c was stained with anti-cytochrome c antibody. Arrows indicate the diffused cytochrome c staining (upper panel). The release of cytochrome c was analyzed by immunofluorescence in HeLa cells after treatment with MTD peptides (5 µM) (lower panel).

(C) HeLa cells were pre-treated with zVAD-fmk (25 µM) or IDN-6556 (25 µM) 1 hour before MTD-peptide treatment. After treatment of 5 µM of R8, ΔR8-MTD, and R8:MTD peptides for 5 hours, cell death was assayed by cell counting kit-8 (Dojindo Molecular Technologies, Rockville, USA).

FIG. 3A-3D. The critical amino acid residues of Noxa MTD in Noxa-induced cell death.

(A) The amino acid sequences of MTDmt1 to MTDmt5 are listed in Table 1. HeLa cells were treated with DMSO or with the indicated peptides at increasing doses (10 µM, 20 µM, or 30 µM). % cell death was determined 10 minutes after treatment by counting the dead cells and survived cells (300 cells per sample) under the light microscope.

(B) HeLa cells were transfected with WT or with the indicated Noxa mutants. 20 hours after transfection cell death was determined by counting the EGFP-positive dead and survived cells under the fluorescent microscope.

(C) NCI-H460 cells were treated with indicated peptides for 2 hours or 5 hours. % cell death was determined as described above.

(D) A549 cells were treated with indicated peptides for 1, 2, or 5 hours. % cell death was determined as described above.

FIG. 4A-4G. MTD peptide induces a calcium spike in the cytosol.

(A-C) HeLa cells were loaded with 3 µM Fluo-4-AM for 30 minutes and then treated with 3 µM of indicated peptides (A: MTD, B: MTDmt3, C: MTDmt5). Fluorescence images and bright-field images were obtained with the laser scanning confocal microscope at 5-second intervals for 5 minutes. Relative fluorescence intensities (F/F0) at two region-of-interests (ROI 1 and 2) were measured at 5-second intervals for 5 minutes.

(D) HeLa cells were treated with the MTD (5 µM) peptide with or without the pretreatment of 10 µM BAPTA-AM for 2 hours. Live cell images were serially acquired at 10-second intervals for 10 minutes and shown at the indicated times. Arrows indicate the appearance of membrane blebbings.

(E-G) HeLa cells were pretreated in calcium free KRB media alone (E), in KRB media with 10 µM 2-APB and 20 µM Ryanodine (F), or in KRB media with freshly made 30 µM CsA (G) for 2 hours. HeLa cells were then loaded with 3 µM Fluo-4-AM for 30 minutes and treated with 3 µM of MTD peptide. Images were obtained with the laser scanning confocal microscope at 5-second intervals for 5 minutes. Relative fluorescence intensities (F/F0) at two region-of-interests (ROI 1 and 2) were measured at 5-second intervals for 5 minutes.

Figure 5A:
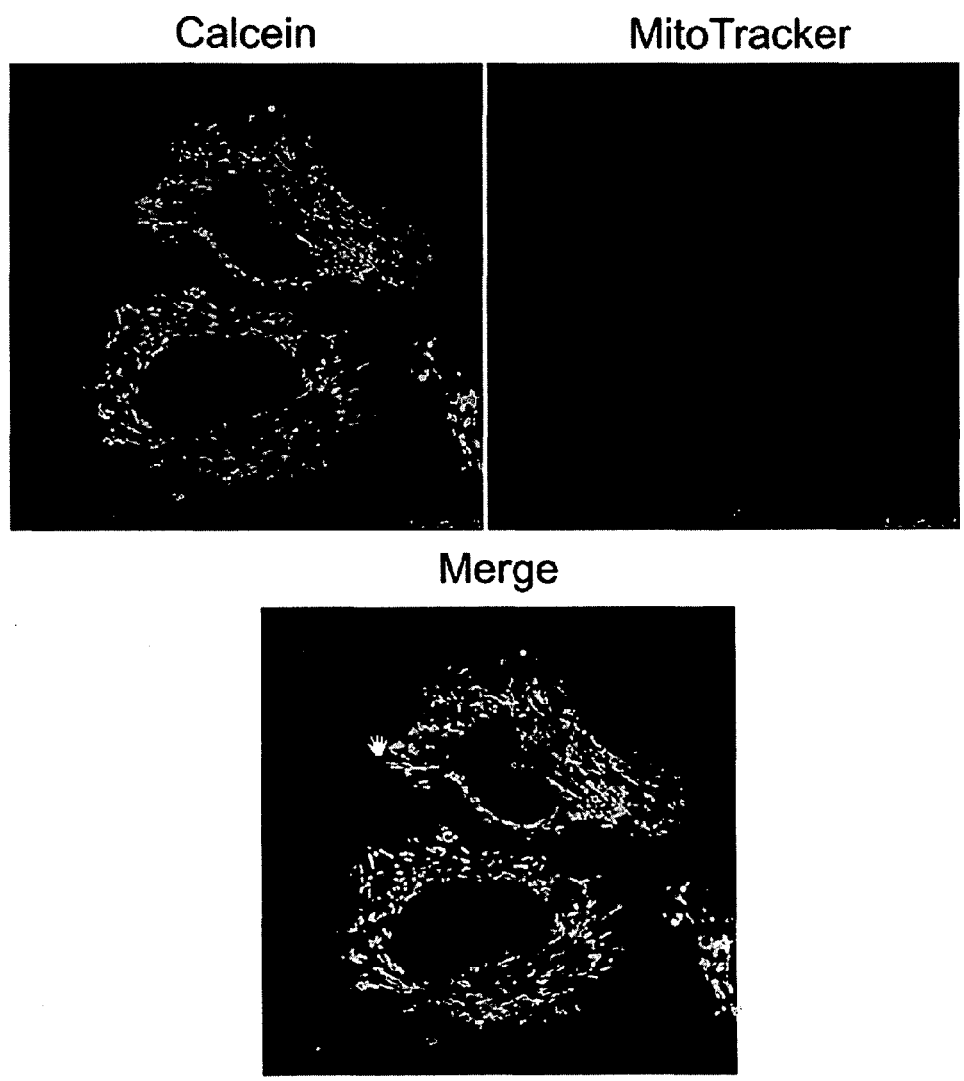
Figure 5B:
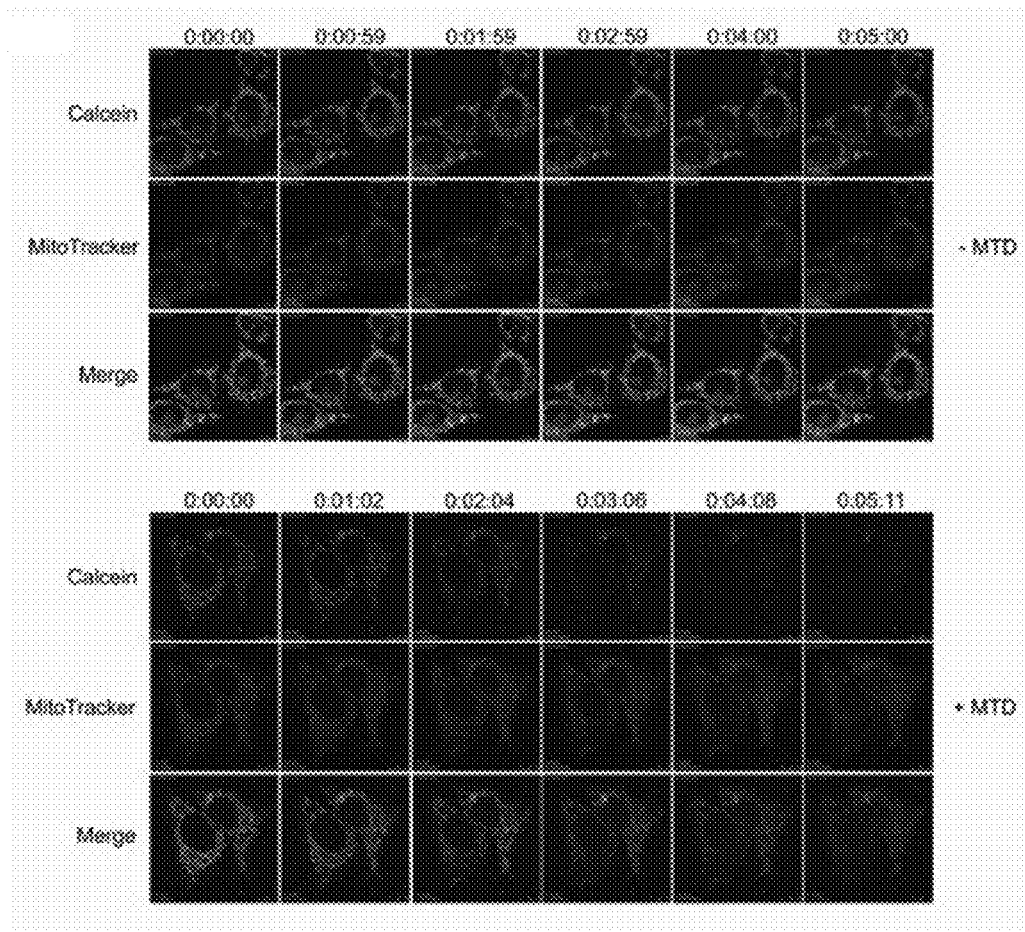

FIG. 5A-5B. The opening of mitochondrial permeability transition pore by MTD peptide.

(A) HeLa cells were loaded with 1 µM Calcein-AM and 2 mM cobalt for 15 minutes, and the mitochondria were stained by adding 25 µM MitoTracker for 2 minutes. The representative image of the calcein signals (green) that were overlapped with MitoTracker (Red) was shown.

(B) Time-lapse images of calcein and MitoTracker signals from HeLa cells that were not treated (top panel) or treated (bottom panel) with MTD peptide were obtained at 10-second intervals for 5 minutes. The representative images at the indicated time points were shown.

FIG. 6A-6D. TU:MTD peptides induces cell death in vitro and in vivo.

(A) CT26 cells were injected subcutaneously into the Balb/c mice. Tumor cells were grown for 7 days, and TU2: MTD peptide (385 µg/mouse) or PBS was intravenously injected through the tail vein (n=10 animals/group) every two days from day 7 to day 19. Tumor volume was calculated as the longest diameter×width2×0.5.

(B) TU3:MTD peptide (230 µg/mouse) or PBS were intravenously injected to the Balb/c mice bearing tumor through the tail vein (n=5 animals/group) every two days from day 8 to day 20. Tumor volume was measured as described above.

(C) Tumors were obtained from the mice treated with PBS, TU2:MTD or TU3:MTD upon sacrificing the mice, and were stained with hematoxylin and eosin. Images (400× magnification) at tumor regions were obtained (left), and the boxed region were enlarged (right).

(D) Images (400× magnification) of liver and kidney from normal mice or mice treated with, PBS, TU2:MTD or TU3: MTD peptides seven times every two days were obtained after stained with hematoxylin and eosin.

FIG. 7. Characteristics of MTD peptide-induced cell death.

(A) HeLa cells were stained with FITC-conjugated Annexin V antibody at 10 minutes after DMSO or MTD treatment. Images were obtained under the confocal microscope.

(B) HeLa cells were stained with SYTOX Green 10 minutes after DMSO or MTD treatment. Images were obtained using confocal microscope.

(C) HeLa cells were treated with DMSO or MTD peptides (10 µM) for 10 minutes or 30 minutes in the serum-free culture medium. After treatment, culture mediums were collected. Proteins in the conditioned media were precipitated by 2.5 vol. of methanol and 0.1 vol. of 5M NaCl. Precipitates and cell lysates were subjected to SDS-PAGE and western blot analysis with anti-HMGB1 antibody (R&D systems, Minneapolis, Minn.).

(D) Isolated mouse liver mitochondria were treated with buffer (NT), MTD peptide (10 µM), or MTDmt5 peptide (10 µM), and then incubated for 1 hour at 30° C. Mitochondria were harvested by centrifugation (10,000×rpm) and then processed for transmission electron microscopy. Images (upper panel) were obtained with 7,000× magnification, and the relative mitochondrial sizes (lower panel) were calculated by measuring the diameters of about 40 individual mitochondria.

(E) After treatment with the MTD peptide, MTDmt4, or MTDmt5 (5 µM) in HeLa cells, cell lysates were prepared at indicated times. Equal amounts of proteins were subjected to the SDS-PAGE and blotted onto PVDF membrane. After blocked with 5% nonfat milk in TBST (10 mM Tris-HCl, pH 7.5, 100 mM NaCl and 0.1% Tween-20), the membrane was probed with anti-caspase-3 (SantaCruz Biotechnology, Inc., Santa Cruz, Calif., USA), anti-caspase-8 (Cell signaling technology, Beverly, Mass., USA), anti-caspase-9 (SantaCruz Biotechnology, Inc., Santa Cruz, Calif.), anti-XIAP (Upstate Biotechnology, Dundee, United Kingdom), or anti-Bid (home-made) antibodies. Anti-actin antibody (Chemicon International, Inc., Temecula, Calif., USA) was used as equal loading control.

FIG. 8A-8D. The critical amino acid residues of Noxa MTD in Noxa-induced cell death.

(A) HeLa cells were transfected with either WT Noxa, 4Lmt (L42A, L43A, L45A, L49A), or 5Lmt (L29A, L42A, L43A, L45A, L49A) constructs. At the indicated times after transfection, cell death was determined by counting the EGFP-positive dead cells with morphological changes under the fluorescent microscope.

(B) HeLa cells were co-transfected with the pDsRed2-Mito and either Noxa 4Lmt or Noxa 5Lmt. 18 hrs after transfection the mitochondrial morphology was observed under the laser confocal microscope.

(C) pEGFP-Noxa WT, L42A, L43A, L45A, L49A (1 µg) were cotransfected with pcDNA3-Mcl-1 (1 µg) into 293T cells, and cells were further cultured for 26 hours. The cell lysates prepared with the buffer (20 mM HEPES, 150 mM NaCl, 1 mM EDTA, 1 mM EGTA, 1% Triton-X-100, 1% sodium deoxycholate, proteinase inhibitor cocktails) were incubated with anti-EGFP (for Noxa) for 2 hours. The protein (A+G) conjugated with agarose bead was added and further incubated for 1 hour at room temperature. Precipitates or input lysates were subjected to SDS-PAGE and analyzed by western blots using anti-EGFP (for Noxa) and anti-Mcl-1 antibodies.

(D) HeLa cells were treated with indicated amounts of MTD peptide for 1 hour, 2 hours, or 5 hours. % cell death was calculated by counting the dead cells and survived cells (200 to 500 cells per sample) under the light microscope. Data represent the means±SD of three independent experiments.

FIG. 9A-9D. TU:MTD peptides induces cell death in CT26 cells, and reduce tumor weights.

(A) CT26 cells were treated with 10 µM MTD, TU1:MTD, TU2:MTD, or TU3:MTD peptides, and bright field images for indicated peptides were obtained at indicated time points. Representative images of at least 3 individual experiments were presented.

(B) CT26 cells were injected subcutaneously into the Balb/c mice. Tumor cells were grown for 7 days, and TU2:MTD peptide (385 µg/mouse) or PBS was intravenously injected through the tail vein (n=10 animals/group) every two days from day 7 to day 19. Tumor weights were measured after mice were sacrificed.

(C) TU3:MTD peptide (230 µg/mouse) or PBS were intravenously injected to the Balb/c mice bearing tumor through the tail vein (n=5 animals/group) every two days from day 8 to day 20. Tumor weights were measured as described above.

(D) Images (100× magnification) of dermis and epidermis region of normal skin or adjacent to tumor treated with PBS, TU2:MTD or TU3:MTD peptides were obtained after stained with hematoxylin and eosin.

Figure 10:
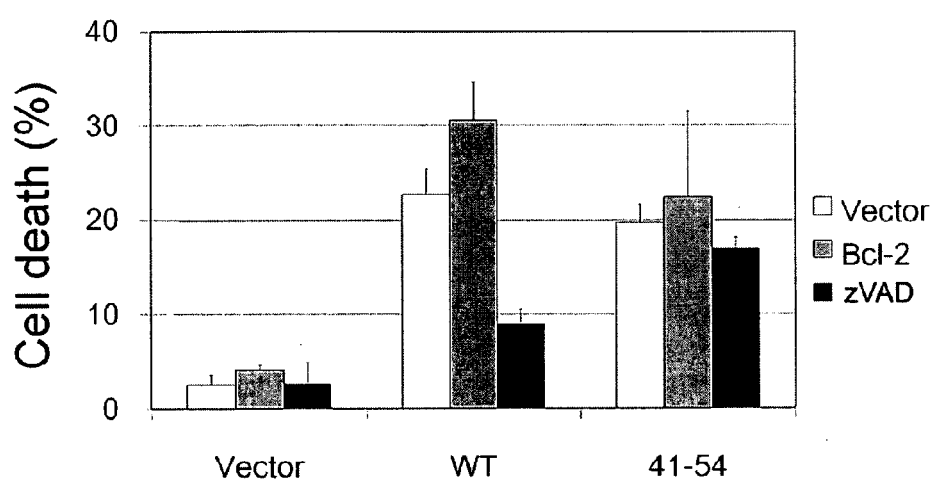

FIG. 10. Release of HMGB1 into the media by MTD peptide, and no inhibition of MTD-induced cell death by caspase inhibitor.

HeLa cells were transfected with EGFP-Noxa WT and 41-54 in combination with Bcl-2 expression plasmid or in the presence of zVAD-fmk (25 µM). 18 hours after transfection, cell death was determined by counting EGFP-positive dead cells with morphological changes using the fluorescent microscope. Data represent an average±SD of three experiments each with 200 total cells counted.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Cell Culture

HeLa cells were maintained in DMEM (Dulbecco's Modified Eagle's Medium) supplemented with 10% fetal bovine serum, 100 units/ml of penicillin, and 100 µg/ml of streptomycin at 37° C. with 5% $CO_2$ in a humidified incubator.

Cloning and Mutagenesis

Deletion constructs of Noxa (Phorbol-12-myristate-13-acetate-induced protein 1) were described previously (8). Site-directed mutagenesis was performed using PCR primers to convert leucine residues at positions 29, 42, 43, 45, and 49 of Noxa to alanine as follows.

For L29A conversion, the first PCR was performed using following the primers [Noxa 5'-(1)-primer (GAAGATCTATGCCTGGGAAGAAGGCGCGC) plus L29A 3'-primer (CTCCAAATCTCCTGGCTTGAGTAGCACACTC) and L29A 5'-primer (GAGTGTGCTACTCAAGCCAGGAGATTTGGAG) plus Noxa 3'-(54)-primer (CGAATTCTCAGGTTCCTGAGCAGAAGAG)] and pEGFP-Noxa as a template, and then a second PCR was carried out using the Noxa 5' (1) primer plus Noxa 3' (54) primer with the first PCR products as a template. The second PCR products were digested with BglII and EcoR1 and cloned into pEGFP-c1.

For L42A, L43A, and L45A conversions, PCRs were carried out using Noxa 5' (1) primer plus L42A 3'-primer (TTTGGATATCAGATTCAGAGCTTTCTGCCGGAA), Noxa 5'-(1)-primer plus L43A 3'-primer (TTTGGATATCAGATTCGCAAGTTTCTGCCGG), and Noxa 5'-(1)-primer plus the L45A 3'-primer (TTTGGATATCGCATTCAGAAGTTTCTGCCGG), respectively, and the PCR products were then digested with BglII and EcoRV and cloned into pEGFP-Noxa (1-54) digested with BglII and EcoRV.

For L49A conversion, PCR was carried out using Noxa 5'-(1)-primer plus L49A 3'-primer (CGAATTCTCAGGTTCCTGAGCAGAAGGCTTTGGATATCAGATTCAG), and then digested with BglII and EcoR1 followed by cloning it into pEGFP-c1 at BglII and EcoR1 sites. For 4Lmt and 5Lmt, wild type Noxa (WT Noxa) and L29A constructs, respectively, were used as templates for PCRs done with the Noxa 5' primer plus the 4mt 3'-primer (GTTTGGATATCGCATTCGCAGCTTTCTGCCGGAAG). PCR products digested with BglII and EcoRV were cloned into the vector generated from pEGFP-Noxa L49A.

All Noxa mutant constructs were confirmed by DNA sequence analysis.

Peptide Synthesis

In order to synthesize the peptides of the examples, manual Fmoc synthetic method using 0.25 mmol unit was basically adopted. In detail, resin was washed using 4× DMF, blended with 10 ml of 20% piperidine/DMF solution for 1 min, and separated to remove supernatant. The resulting resin was mixed again with 10 ml of 20% piperidine/DMF solution, shaken for 30 min, and then washed using 4× DMF. Ninhydrin test was performed to see whether piperidine remains or not. Resin appears blue without piperidine. For a coupling step, a solution comprising 1 mmol of Fmoc-amino acid, 2.1 ml of 0.45 M HBTU/HOBT (1 mmol), and 348 µl of DIEA (2 mmol) was prepared. The resin was mixed with the solution and stirred for 30 minutes. Then the resin was separated from the solution and washed using 4× DMF.

The coupling step was repeated for several times to link the next amino acids. The resulting peptides were_purified by HPLC (High-performance liquid chromatography, Peptron, Daejeon Korea), suspended in 50% dimethyl sulfoxide (DMSO) at 0.5 mM, and stored at −20° C.

Peptide nomenclature and sequences used in the examples are listed in Table 1. ΔR8 indicates deletion of eight arginine amino acid residues.

TABLE 1

Peptide nomenclature and sequences

| Peptides | Sequences | SEQ ID NOs |
|---|---|---|
| NoxaBH3 | RRRRRRRRGECATQLRRFGDKLNF | 8 |
| NoxaBH3MTD | RRRRRRRRGECATQLRRFGDKLNFRQKLLNLISKLF | 9 |
| MTD | RRRRRRRRGRQKLLNLISKLF | 10 |
| MTD2 | RRRRRRRRGRGKALNLISKLF | 11 |
| MTD3 | RRRRRRRRGRGKLAALISKLF | 12 |
| MTD4 | RRRRRRRRGRGKLLNLIAALF | 13 |
| MTD5 | RRRRRRRRGRGKALNLIAALF | 14 |
| ΔR8:MTD | KLLNLISKLF | 1 |
| MTDmt1 (KL41, 42AA) | RRRRRRRRGRQAALNLISKLF | 15 |
| MTDmt2 (LN43, 44AA) | RRRRRRRRGRQKLAALISKLF | 16 |
| MTDmt3 (LI45, 46AA) | RRRRRRRRGRQKLLNAASKLF | 17 |

TABLE 1 -continued

Peptide nomenclature and sequences

| Peptides | Sequences | SEQ ID NOs |
|---|---|---|
| MTDmt4 (SK47, 48AA) | RRRRRRRRGRQKLLNLIAALF | 18 |
| MTDmt5 (LF49, 50AA) | RRRRRRRRGRQKLLNLISKAA | 19 |
| TU1:MTD | CNGRCGGKLLNLISKLF | 20 |
| TU2:MTD | CNGRCVSGCAGRCGGKLLNLISKLF | 21 |
| TU3:MTD | CGNKRTRGCGGKLLNLISKLF | 22 |

Measurement of Intracellular Calcium

For $Ca^{2+}$ measurements in the cytosol, HeLa cells were cultured in an Lab-Tek™ Chamber glass slide and loaded with Fluo-4-AM (Fluo-4-acetoxymethyl ester) at a final concentration of 3 µM for 30 minutes, followed by washing with PBS (Phosphate buffered saline) at pH 7.4 and the addition of fresh $Ca^{2+}$-free Krebs-ringer modified buffer (KRB: 125 mM NaCl, 5 mM KCl, 1 mM $Na_3PO_4$, 1 mM $MgSO_4$, 5.5 mM glucose, and 20 mM HEPES, pH 7.4, at 37° C.) containing the indicated peptides. Time-lapse images were obtained at 488 nm excitation with the Argon laser scanning confocal microscope (Leica TCS SP5 Microsystems, Mannheim, Germany) at 10-second intervals for 5 minutes to visualize Fluo-4-AM.

Cobalt-Quenched Calcein Assay

HeLa cells were loaded with 1 µM Calcein-AM and 2 mM cobalt in serum-free DMEM for 15 minutes, followed by adding 25 µM MitoTracker for 2 minutes to stain the mitochondria. Then, HeLa cells were briefly washed with HBSS (Hank's Buffered Salt Solution) and were treated with MTD peptide in calcium-free media containing 10% FBS (Fetal bovine serum). Time-lapse images were obtained at 10-second intervals for 10 minutes.

Cell Death Assay

The percentage of cell death was determined by counting EGFP-positive dead cells with morphology using the fluorescent microscope. Minimally, 300 cells in three separate fields were counted for each measurement.

Syngeneic Animal Tumor Model

We followed the university's institutional guidelines and regulations for animal experiments. Tumors were established in Balb/c mice by subcutaneous injection of CT-26 cells (1.5× $10^5$ cells) into the mouse as described (14). Tumor volume was calculated as length×width$^2$×0.5. Tumor cells were grown for 7 to 8 days, and TU2:MTD peptide (385 µg/mouse), TU3:MTD peptide (230 µg/mouse), or PBS was intravenously injected through the tail vein every two days until the mice were sacrificed.

Immunoprecipitation Assay pEGFP-Noxa WT, pEGFP-Noxa L42A, pEGFP-Noxa L43A, pEGFP-Noxa L45A, and pEGFP-Noxa L49A (1 µg) were cotransfected with pcDNA3-Mcl-1 (1 µg) into 293T cells, and cells were further cultured for 26 hours. The cell lysates were prepared with the buffer containing 20 mM HEPES, 150 mM NaCl, 1 mM EDTA, 1 mM EGTA, 1% Triton-X-100, and 1% sodium deoxycholate in the presence of proteinase inhibitor cocktails. The primary antibody against EGFP was incubated with the cell lysates for 2 hours. The protein (A+G) conjugated with agarose bead was added and further incubated for 1 hour at room temperature. Upon centrifugation, the pellets were washed with the buffer several times.

Transmission Electron Microscopy

Jurkat cells or isolated mitochondria treated with MTD peptides were harvested by centrifugation and fixed with 2.5% glutaraldehyde for 2 hours followed by washing with 0.2 M sodium cacodylate buffer (pH 7.2) three times for 10-20 minutes. Fixation step was repeated overnight and washed with 0.2 M sodium cacodylate buffer three times. Samples were dehydrated with following sequential solutions 60% ethanol, 70% ethanol, 80% ethanol, 90% ethanol, 95% ethanol, and 100% ethanol twice for 20 minutes at 4° C., and then infiltrated by propylene oxide three times for 20 minutes. Samples were embedded with the mixture of propylene oxide and epon for 6 hours. Electron microscopic images were obtained using the Hitachi H-7600 electron microscope (80 kV, Hitachi, Tokyo, Japan). Mitochondria were isolated from mouse liver as previously described (1).

Results

Mitochondrial Targeting Domain of Noxa has Cell Death-Inducing Activity

Figure 1A:
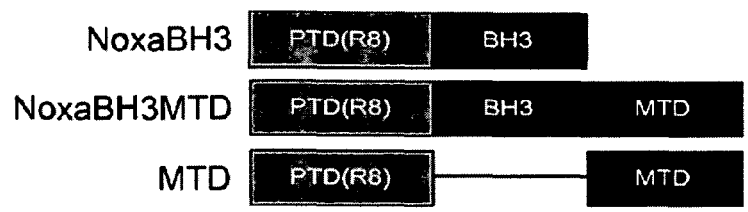
FIGS. 1A-1E. Induction of cell death by the MTD.
Figure 1B:
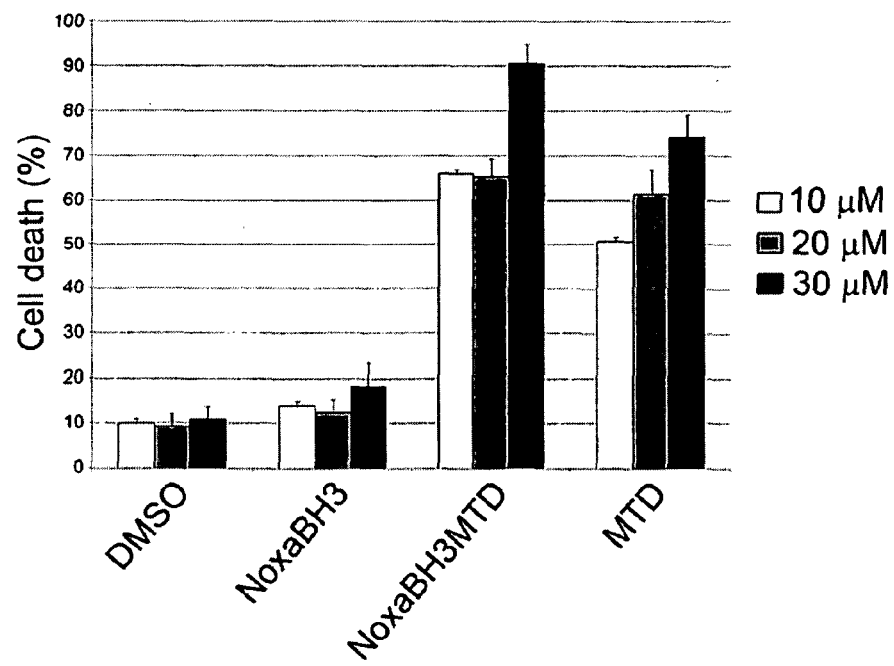
Figure 1C:
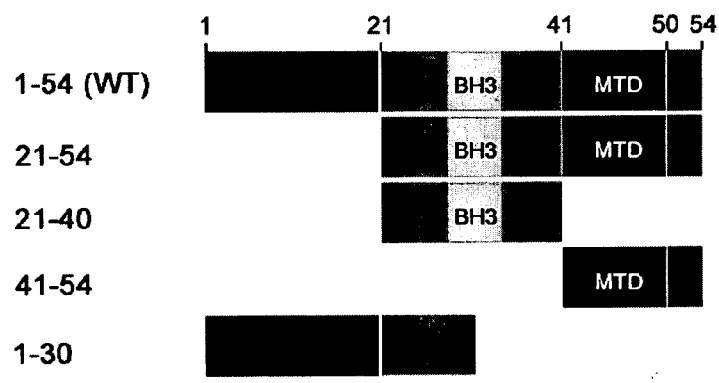
Figure 1D:
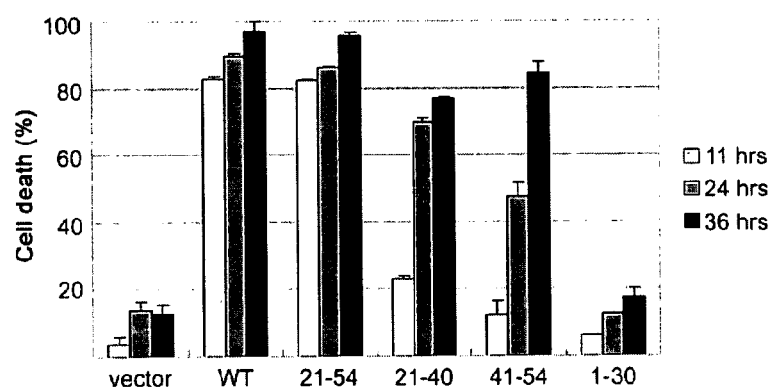

Previously we defined the C-terminal region (41-50) of Noxa as the mitochondrial targeting domain (MTD) (8). Because the BH3 domain of BH3-only proteins exerts its influence on the mitochondria, we hypothesized that the BH3 domain could be efficiently delivered to the mitochondria if fused with the MTD, such that the chimeric peptide would have the more potent killing activity. Peptides of the NoxaBH3 domain alone, NoxaMTD alone, and the BH3 domain fused with the NoxaMTD were synthesized (Table 1, FIG. 1A), and were tested for their ability to induce cell death, showing that the MTD alone had the comparable cell death-inducing activity to NoxaBH3MTD peptide (FIG. 1B). It indicates that MTD in Noxa have a killing activity. Thus, we have checked the cell killing activities of Noxa deletion mutants in HeLa cells (FIG. 1C). Over-expression of WV Noxa and 21-54, which contained both the BH3 domain and MTD, induced cell death within 11 hrs in HeLa cells. 41-54, which contained only MTD, and 21-40, which contained only the BH3 domain, induced little cell death within 11 hrs; also, 1-30, which did not contains any domains, had no effect on cell death in HeLa cells (FIG. 1D). These results are consistent with the previous results showing that both the BH3 domain and the MTD are required for Noxa-induced cell death (8). However, with increasing time, strong cell death-inducing activity was observed with the 41-54, indicating that MTD alone has cell death-inducing activity. Over-expression of the 21-40 resulted in strong cell death-inducing activity at 24 hrs and 36 hrs (FIG. 1D). These results indicate that both the BH3 domain and the MTD of Noxa possess the cell killing activities.

Figure 7A:
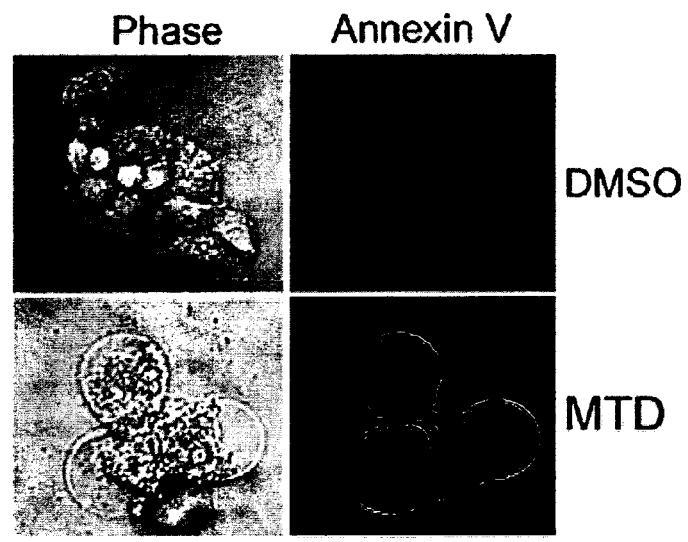
Figure 7B:
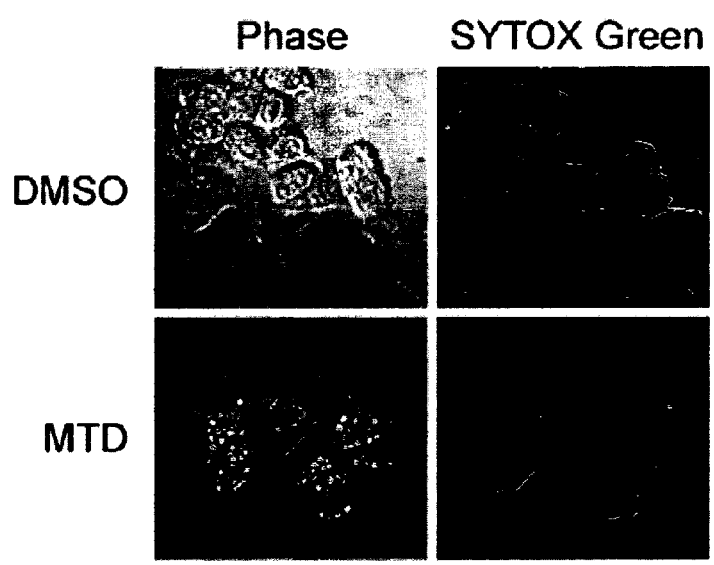
Figure 7C:
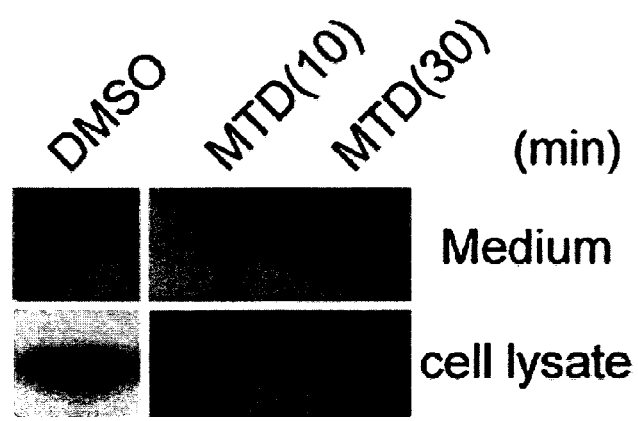

The characteristics of cell death induced by MTD peptide were quite different from the classical apoptotic characteristics. Unlike the membrane shrinkage of apoptotic cells induced by TRAIL, bubble-like structures of dying cells treated with MTD peptide were observed (FIG. 2A). MTD peptide-treated cells were stained with annexin V and SYTOX Green (FIGS. 7A and 7B), and showed the swollen cytoplasmic membrane, a typical morphology of necrosis. Also, ultrastructural changes analyzed by transmission electron microscopy revealed the swollen mitochondria, the enlarged nucleus and cell membrane swelling by MTD peptide, indicating that MTD peptide induces necrosis rather than apoptosis (FIG. 2A). Because high mobility group B1 (HMGB1) can be released to outside of cells undergoing necrosis (15, 16), HMGB1 should be released into the media when HeLa cells are treated with MTD peptide. Indeed, HMGB1 was significantly released to the media within 10 to 30 minutes after MTD peptide treatment, whereas HMGB1 was retained in cells without MTD peptide treatment (FIG. 7C).

Figure 7D:
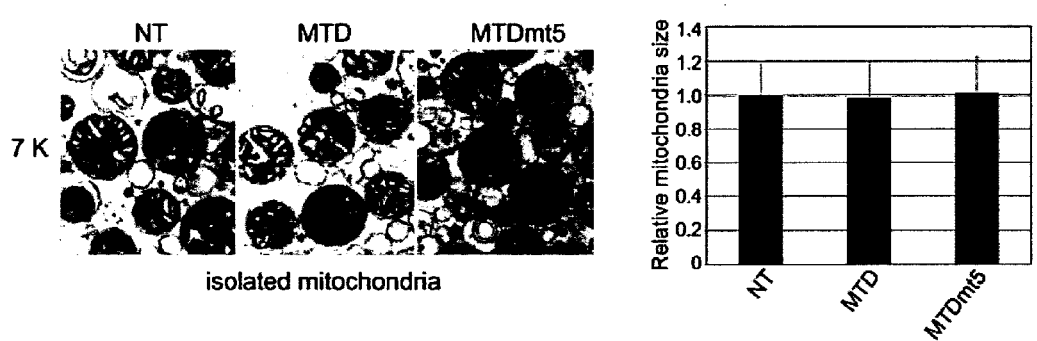
Figure 7E:
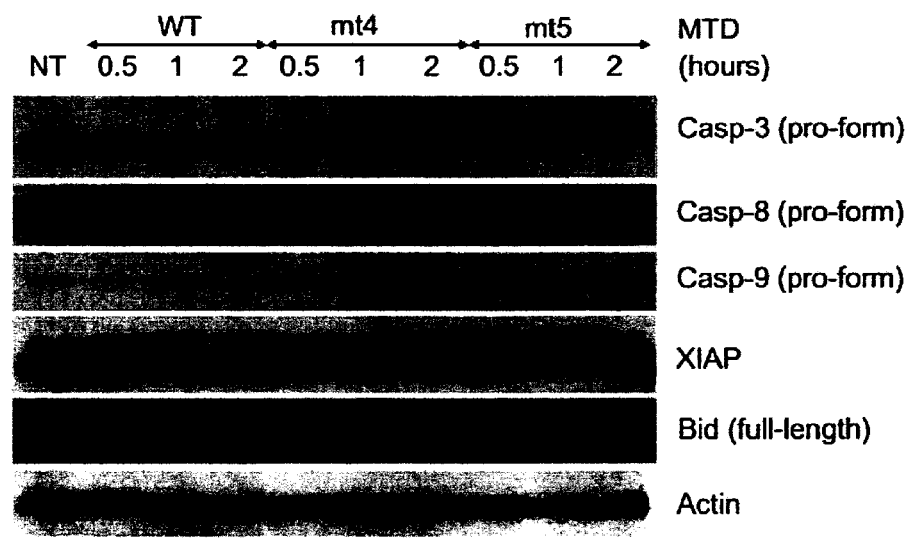

We further tested whether MTD peptide directly damages the mitochondria. Cytochrome c was not released from the mitochondria to the cytosol in cells treated with MTD peptide, whereas Noxa WT was able to release the cytochrome c from mitochondria (FIG. 2B). Also, MTD peptide-induced cell death could not be blocked by the pan-caspase inhibitor zVAD-fmk or IDN-6556 (FIG. 2C), supporting the view that MTD peptide-induced cell death is mediated by a non-caspase process. The isolated mitochondria treated with MTD peptide and the mutant MTDmt5 peptide (mutant peptide, no killing activity (FIG. 3A)) did not show any morphological changes or mitochondrial size changes (FIG. 7D). Moreover, R8 or ΔR8:MTD could not cause cell death (FIG. 2C), suggesting that MTD peptide needs to pass through the cytoplasmic membrane and then activates some cytosolic factor(s) to initiate the cell death. Caspases were not activated by the MTD, the mutant MTDmt4 (mutant peptide maintaining the killing activity (FIG. 3A)) or MTDmt5 peptides (FIG. 7E). It is further confirmed by the facts that cell death induced by Noxa 41-54 transfection into HeLa cells was not inhibited by zVAD-fmk, whereas cell death induced by Noxa WT transfection was significantly inhibited by zVAD-fmk (FIG. 10). Together, these results support the view that Noxa MTD induces the necrotic-like cell death in a caspase-independent manner.

Substitution Variants of MTD Peptide Retain Cell Death-Inducing Activities

Figure 1E:
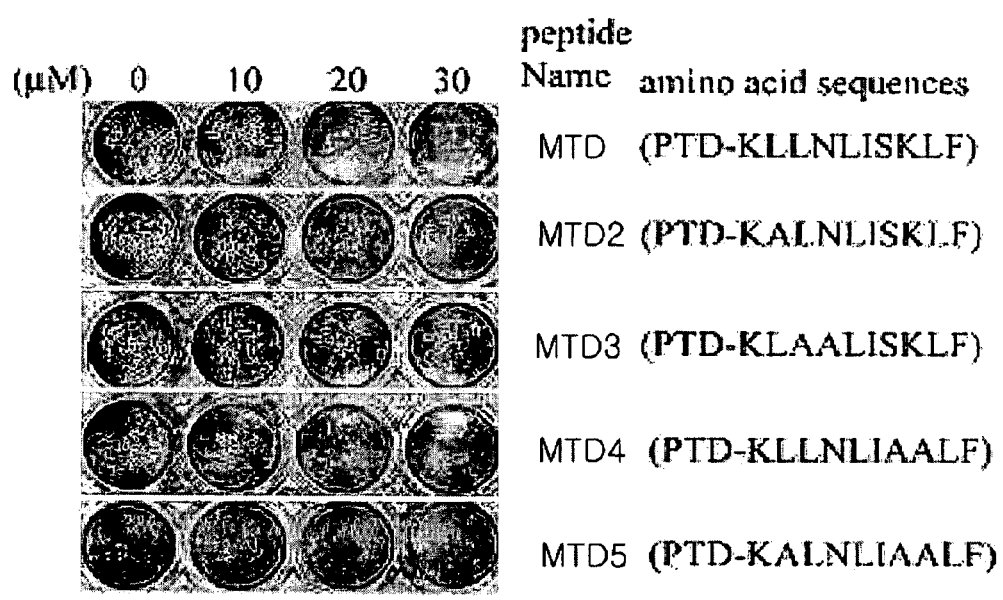

In order to examine whether MTD peptide variants retain the cell-killing activity or not, several MTD peptide variants in Table 1 (MTD 2-5) were prepared by the procedure described previously. Then, we have checked the cell killing activities of these MTD substitution mutants in HeLa cells and illustrated the experimental data in FIG. 1E. As a result, MTD 2 (substituted in one residue), MTD 3 (substituted in two residues), and MTD 5 (substituted in three residues) induced the cell death successfully, though the cell-killing activities were slightly decreased compared with MTD peptide. MTD 4 (substituted in two residues) showed the more outstanding cell-killing activity than MTD peptide did.

Leucine Residues in the MTD are Critical to Cell Death-Inducing Activity

Figure 3A:
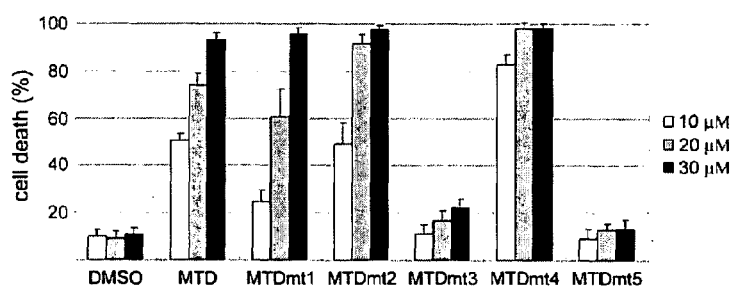
Figure 3B:
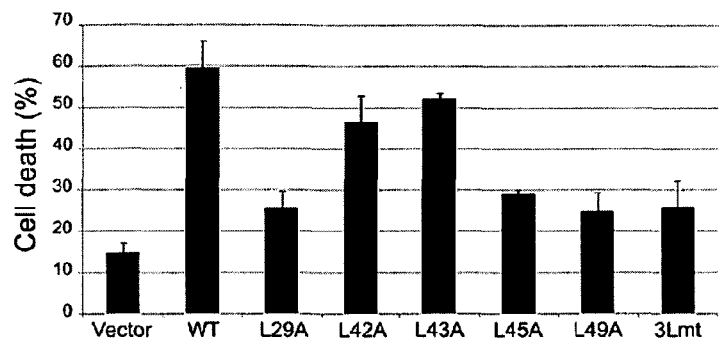

To determine the critical amino acid(s) in MTD responsible for the cell death, we introduced scanning mutations (Table 1) in MTD peptide. MTDmt1 and MTDmt2 peptides exhibited similar cell death-inducing activities in HeLa cells. MTDmt3 and MTDmt5 peptides completely lost their cell death-inducing activities (FIG. 3A). MTDmt3 and MTDmt5 peptides commonly contain leucine residues, suggesting that leucine residues in the MTD may play a crucial role in the cell death-inducing activity.

Figure 8A:
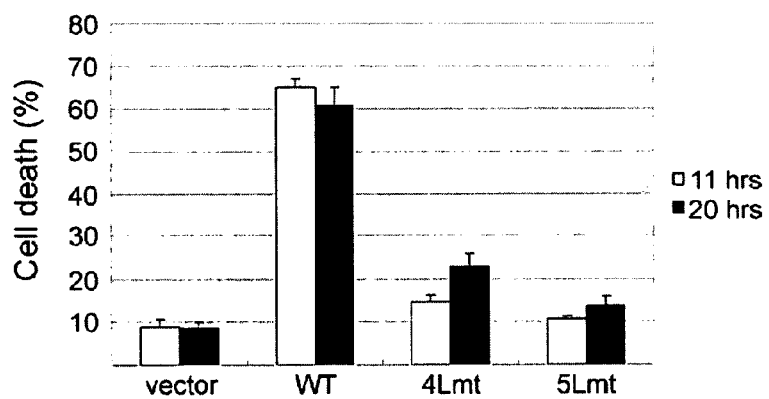
Figure 8B:
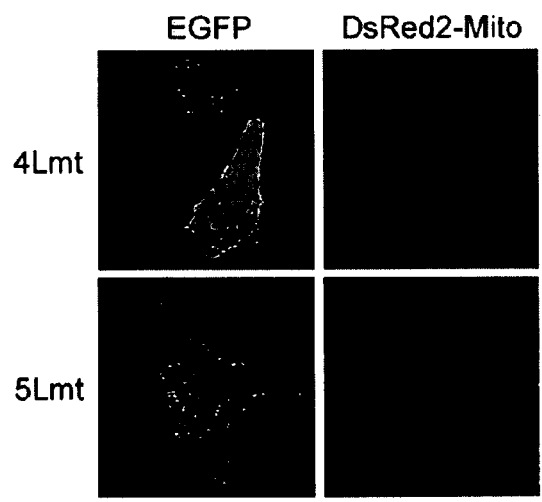

To determine which of the leucine residues in the MTD are critical for its function, a 4Lmt Noxa mutant was generated to contain 4 substitution mutations (L42A, L43A, L45A, and L49A) at the 4 leucine residues in the MTD. Also, a 5Lmt Noxa mutant was generated that contained the same mutations in the MTD as 4Lmt and an additional mutation (L29A) in the BH3 domain, since the leucine residue in the Noxa BH3 domain was shown to be critical for its killing activity (6). While WT Noxa induced more than 60% of cell death, 4Lmt and 5Lmt almost completely lost all of the cell death-inducing activity. The loss of cell death-inducing activity in 4Lmt and 5Lmt was mainly due to the loss of Noxa mitochondrial localization (FIGS. 8A and 8B). To further determine the critical residues in the MTD, we constructed single amino acid substitution (leucine residue to alanine residue) in either the MTD (L42A, L43A, L45A, and L49A) or in the BH3 domain (L29A), or triple substitution (3Lmt) in both MTD (L45A and L49A) and BH3 domain (L29A) and assessed the effect on the cell death-inducing activity. First, we tested Noxa mitochondrial localization in these mutants. The Noxa point mutants (L42A, L43A, L45A, and L49A) maintained the typical mitochondrial localization of Noxa based on confocal microscopic image analysis. Noxa L29A, L45A, L49A, and 3Lmt mutants had remarkably reduced the cell death-inducing activities (FIG. 3B), indicating that both 45 and 49 leucine residues in the MTD and 29 leucine in the BH3 domain play a key role in the Noxa-induced cell death.

Figure 8C:
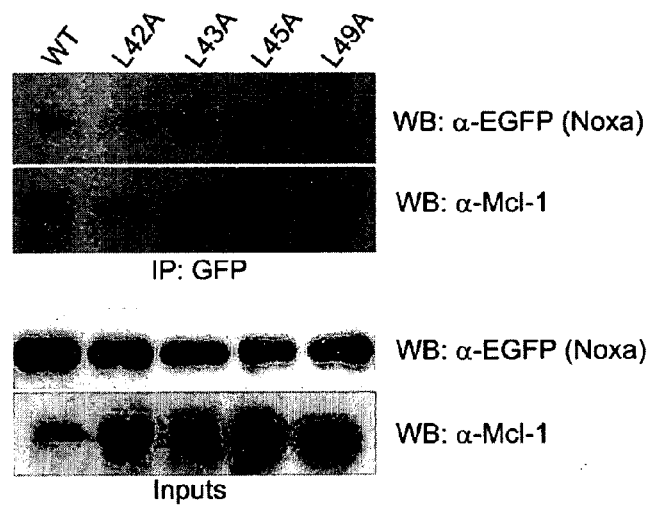
Figure 8D:
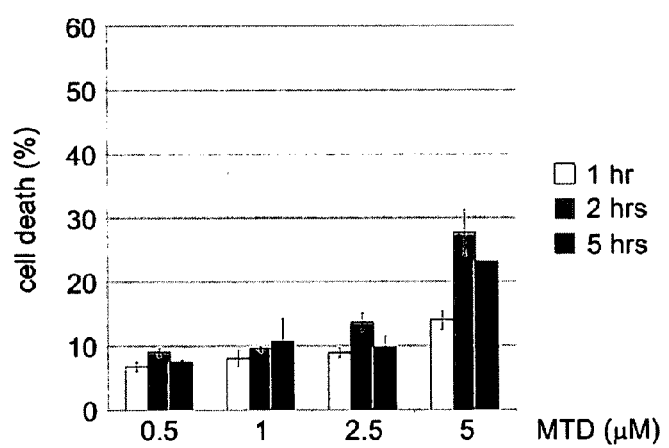

Mcl-1 has been known to inhibit Noxa-induced cell death by binding to BH3 domain of Noxa (12, 17, 18). To test whether the point mutations in MTD region of Noxa affects the binding of Noxa to Mcl-1, the interactions between Mcl-1 and Noxa mutants were examined by immunoprecipitation. Noxa mutants in the MTD region maintained their binding abilities to Mcl-1, indicating that the reduced killing activities of L45A and L49A were not due to the loss of Mcl-1 binding activity (FIG. 8C).

Figure 3C:
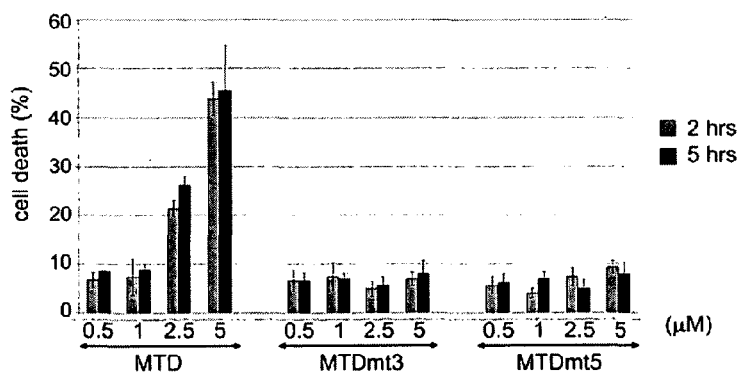
Figure 3D:
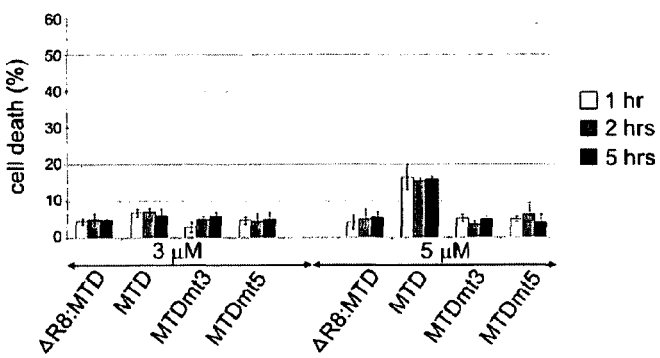

To determine the susceptibilities to MTD peptide in different types of cells, HeLa cells, NCI-H460, or A549 were treated with 0.5 to 5 µM MTD peptide. HeLa cells showed the minimal susceptibility to 5 µM MTD peptide (FIG. 8D); however, NCI-H460 cells were very susceptible to 5 µM MTD peptide but not to 5 µM MTDmt3 or MTDmt5 peptides (FIG. 3C). A549 appears to be very resistant to 5 µM MTD peptide (FIG. 3D). These results demonstrate that different types of cells show the differential susceptibilities to MTD peptide.

Cytosolic Calcium Increase by MTD Peptide Is Associated With the Opening of mPT Pore.

Figure 4A:
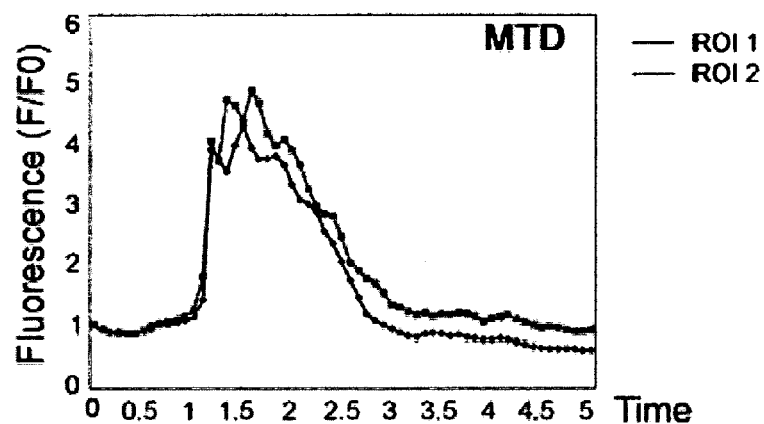
Figure 4B:
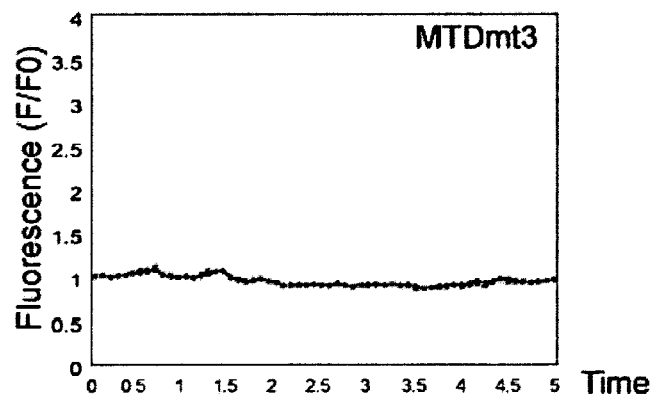

Calcium has been known as a regulator of both cell survival and cell death depending on various cellular signals (19, 20). Thus, we tested whether MTD peptide changes the calcium concentration in the cytosol. The cytosolic calcium changes were monitored using Fluo-4-AM, a fluorescent calcium indicator, in HeLa cells. Cytosolic calcium was substantially increased within 1-3 minutes after MTD peptide treatment, and subsequent decay was observed; however, treatment of HeLa cells with MTDmt3 and MTDmt5 peptides did not induce changes in the cytosolic calcium level (FIG. 4A). This suggests that the cytosolic calcium spike is a key event in MTD peptide-induced cell death. If this rise of cytosolic calcium is the major cause of MTD peptide-induced cell death, the calcium selective chelator BAPTA-AM should inhibit MTD peptide-induced cell death. As predicted, pretreatment of HeLa cells with BAPTA-AM inhibited MTD peptide-induced cell death (FIG. 4B), supporting the idea that the cytosolic calcium spike is a key event in MTD peptide-induced cell death.

Figure 4C:
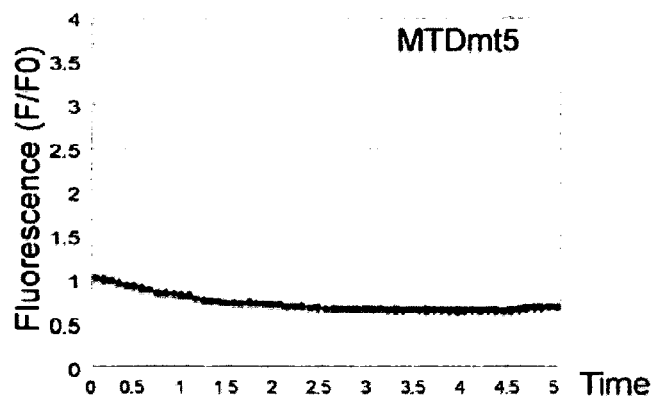
Figure 4D:
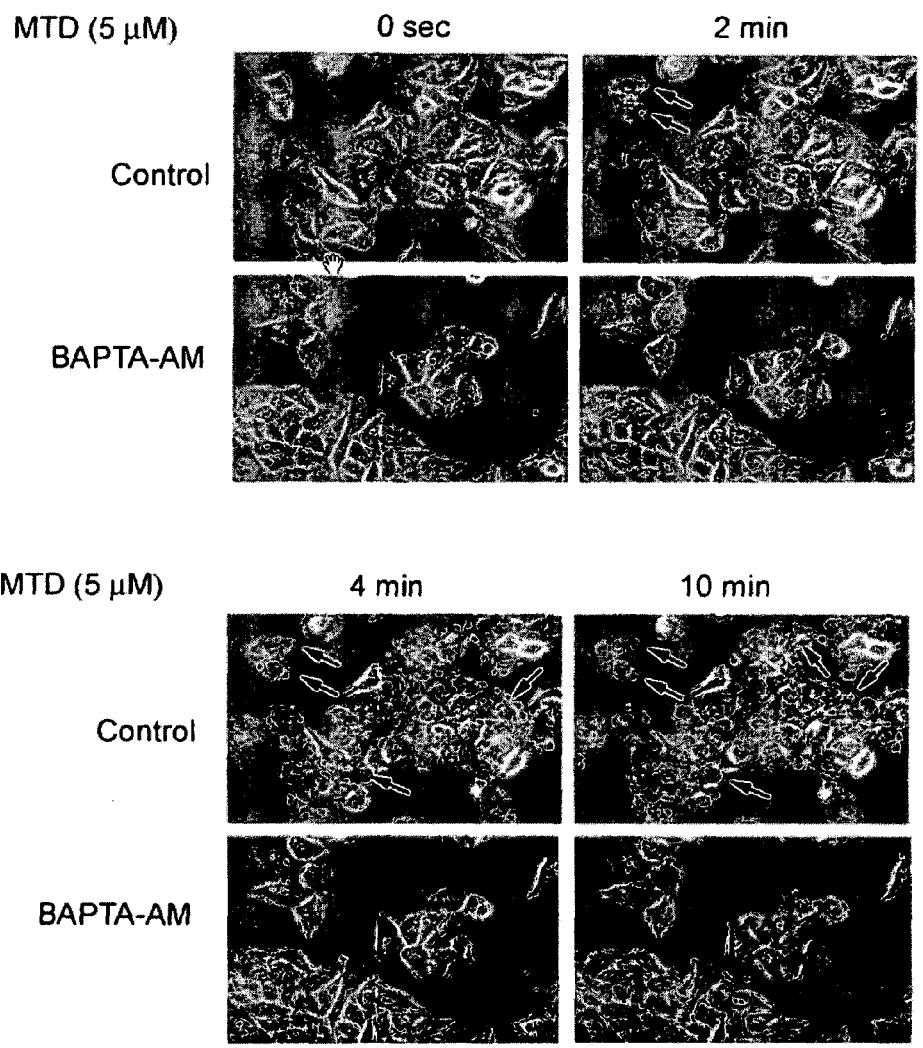
Figure 4E:
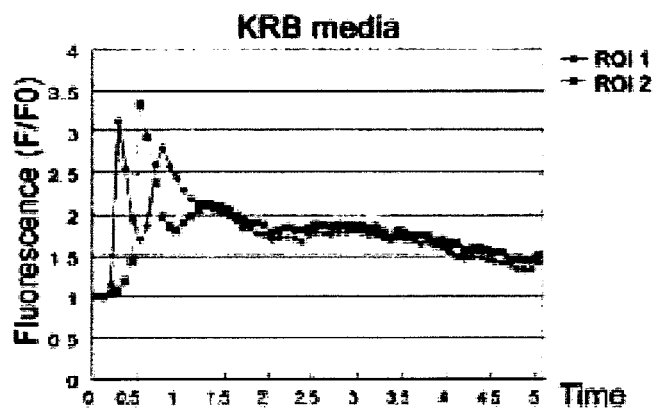
Figure 4F:
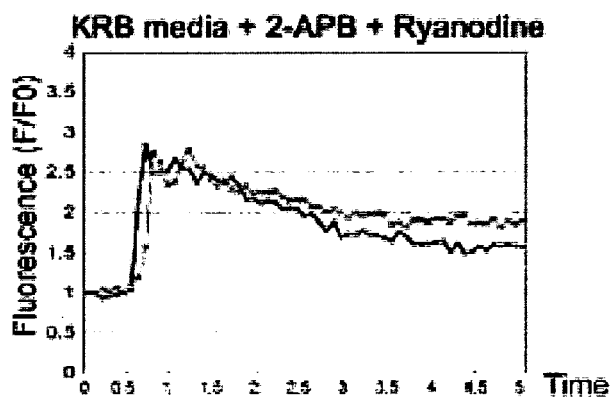
Figure 4G:
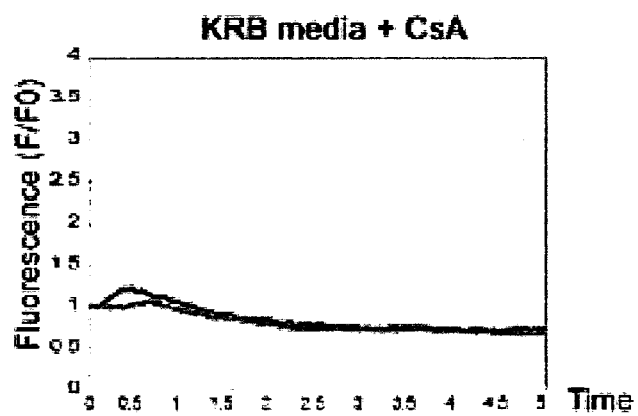

Since the MTD of Noxa is responsible for targeting to the mitochondria and MTD peptide induces the cytosolic calcium spike, we can expect that the cytosolic calcium spike observed during MTD peptide-induced cell death is caused by opening of the mPT pore. However, it is equally possible that the cytosolic calcium increase by MTD peptide is due to the release of calcium from the ER through $IP_3$ receptor ($IP_3R$) and ryanodine receptor (RyR) or the import of calcium from the outside of cells (21). To investigate these possibilities, cytosolic calcium changes by MTD peptide were examined in calcium free KRB media, in the presence of 2-Aminoethoxy-diphenylborate (2-APB) and Ryanodine to block $IP_3R$ and RyR, respectively, or in the presence of cyclosporine A (CsA) to block mPT pore in HeLa cells by time-lapse video confocal microscopy (FIG. 4C). The cytosolic calcium spike was observed in the calcium free KRB media and in the presence of 2-APB and Ryanodine under the KRB media, indicating that the cytosolic calcium spike by MTD peptide is not due to the release of calcium from the ER or the import of calcium from the outside of cells. However, cytosolic calcium spike was not observed in the presence of CsA (FIG. 4C), supporting the idea that the cytosolic calcium spike by MTD peptide is caused by a calcium leak from the mitochondria.

Because CsA is a well-established blocker of mPT pore, the permeability of the mPT pore was directly monitored using cobalt-quenched calcein assay. Non-fluorescent membrane permeable calcein-AM and cobalt were added into HeLa cells, and membrane non-permeable calcein can be spontaneously generated by non-specific esterases in the cytosol and in the mitochondria. The cytosolic calcein signal can be quenched by cobalt; but, mitochondrial calcein signal cannot be quenched because cobalt cannot penetrate the mitochondrial membrane. The mitochondrial calcein signal (Green) was overlapped with the mitochondria specific dye MitoTracker (Red), confirming that cobalt quenched the cytosolic calcein signal but not the mitochondrial calcein signal (FIG. 5A). When the mPT pore opens, cobalt is allowed to enter to the mitochondria through the mPT pore and then quenches the mitochondrial calcein signal. In HeLa cells that were not treated with MTD peptide, the mitochondrial calcein signals were sustained for 5 minutes and were also overlapped with the MitoTracker staining, indicating that the mPT pore is closed (FIG. 5B, upper panel). However, in HeLa cells that were treated with MTD peptide, the mitochondrial calcein signals were significantly decreased within 5 minutes after the treatment of MTD peptide, indicating that the mPT pore is opened by MTD peptide (FIG. 5B, bottom panel). Taken together, these results indicate that MTD peptide opens the mPT pore that allows the mitochondrial calcium to be released into the cytosol.

Tumor-Homing MTD (TU:MTD) Peptides Suppress Tumor Growth.

Figure 6A:
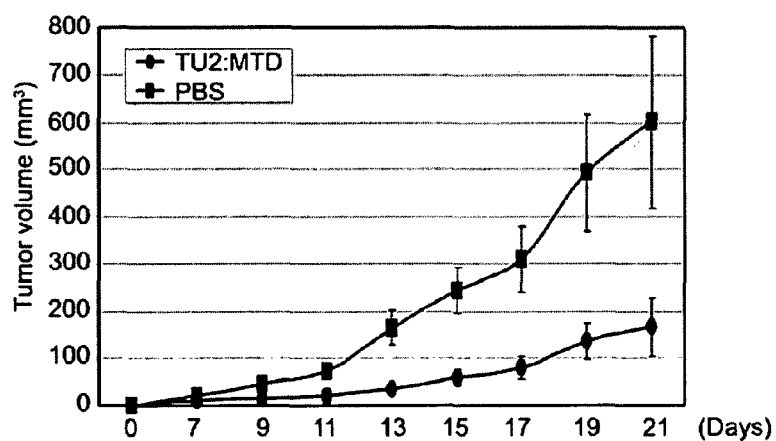
Figure 6B:
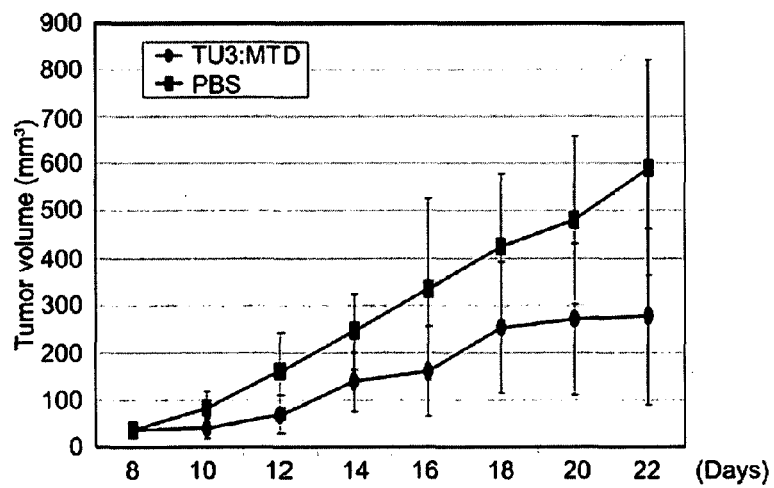
Figure 6C:
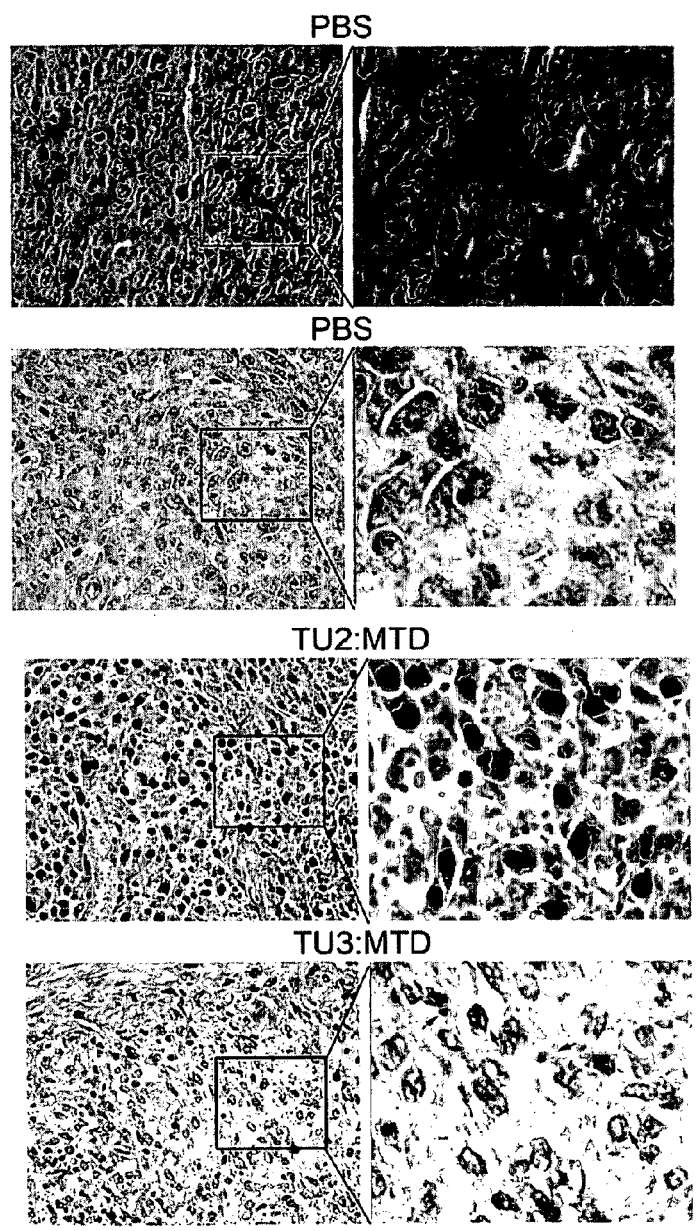
Figure 9A:
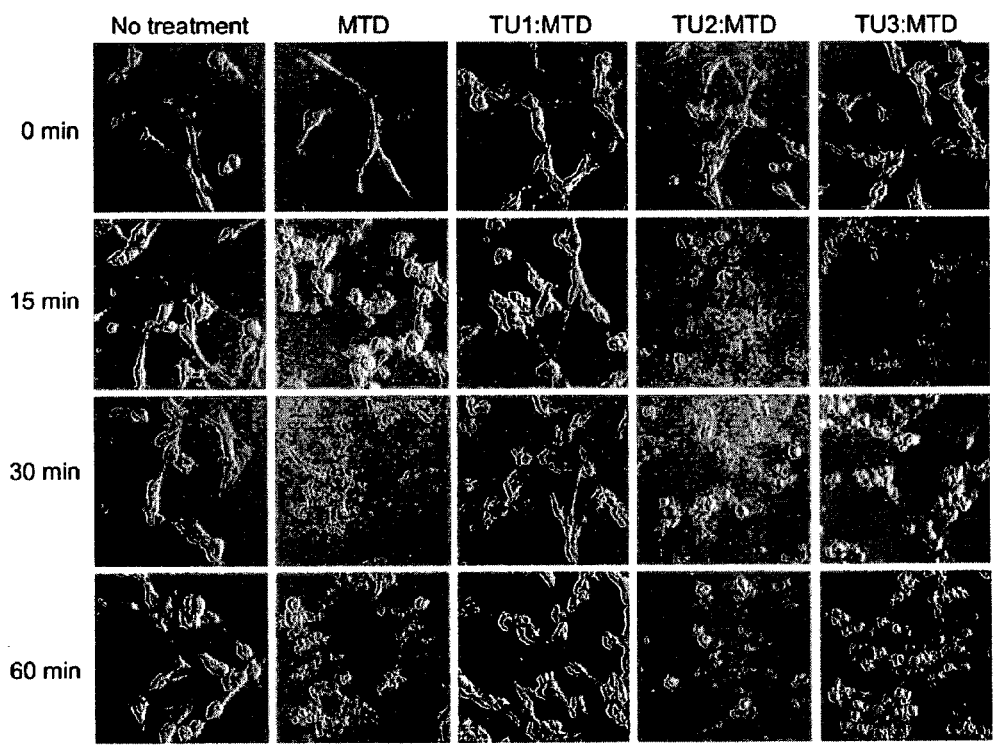
Figure 9B:
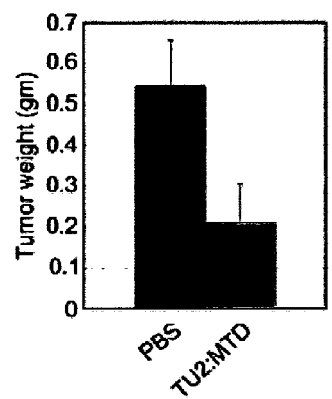
Figure 9C:
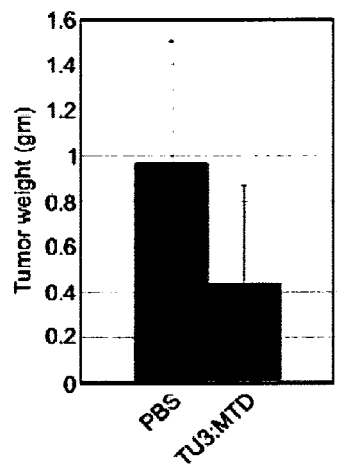
Figure 9D:
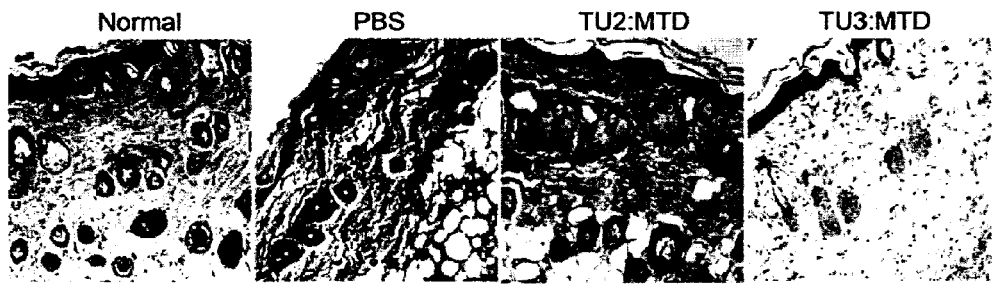

Since PTD (protein transduction domain) peptides bear the basic amino acid residues (e.g., eight arginines) that can penetrate the cytoplasmic membrane of any types of cells, they must be very toxic to animals if systemically injected. Thus, to develop MTD peptide as a tumor killing agent, it should be redesigned as to selectively deliver it to tumor cells or tumor blood vessels. Three tumor-homing MTD (TU:MTD) peptides that bear the tumor vasculature-targeting motifs were synthesized (Table 7) (22, 23), and they were tested for the tumor cell killing activities using CT26 mouse colon carcinoma cells. TU2:MTD and TU3:MTD peptides showed the comparable killing activities to MTD peptide in CT26 cells; however, TU1:MTD peptide did show no or little killing activity, indicating that TU2:MTD and TU3:MTD peptide can penetrate the cytoplasmic membrane of CT26 cells (FIG. 9A). To test whether these peptides have effects on tumor killing or tumor growth in animal, TU2:MTD or TU3:MTD peptides were intravenously injected into Balb/c mice bearing tumors developed by subcutaneous injection of CT26 cells. The mice treated with TU2:MTD or TU3:MTD peptides had significantly smaller tumors than did the mice treated with PBS (FIGS. 6A and 6B). Histochemical examination of tumors revealed that massive cell death of tumor cells was observed in mice intravenously injected with TU2:MTD or TU3:MTD peptides; however, no cell death of tumor cells was observed in mice injected with PBS (FIG. 6C). Dermis and epidermis regions of PBS-injected mice, TU2:MTD peptide-injected mice, or TU3:MTD peptide-injected mice showed similar structures having no or little cell death in these regions; also, microscopic analysis showed no damages in liver and kidney tissues obtained from the mice injected with TU2:MTD or TU3:MTD peptide, and these peptide-injected mice showed no body weight loss (FIGS. 9B-9D and 6D), indicating that TU2:MTD and TU3:MTD peptides do not show apparent toxic effects in mice. Together, these results indicate that TU2:MTD and TU3:MTD peptides selectively target to the tumor regions and induce massive cell death of tumor cells but not normal cells.

Discussion

In summary, we have demonstrated that MTD in the BH3-only protein Noxa per se is a pro-death domain irrespective of BH3 domain through calcium mobilization by activation of mPT pore. We also defined the critical amino acid residues (L45, L49) in the MTD of Noxa for induction of cell death, and further showed that the MTD peptide could be developed as a cancer-treating drug by fusing with the tumor delivery domains.

Apoptosis shows cell shrinkage, chromatin condensation, and generation of apoptotic bodies, whereas necrosis is characterized by cellular swelling, organelle lysis, and cytoplasmic membrane rupture. Although these two modes of cell death are apparently unique and unlikely to be connected, recent studies suggested that these two modes of cell death can be switched each other by the environmental conditions and death stimuli (24-29). With this perspective, it is of interesting to see domains of Noxa in a way that BH3 domain is a key player for apoptosis, and MTD is a key player for necrosis. This view can be supported by the facts that introduction of mutation in BH3 domain of Noxa reduced the apoptosis induced by Etoposide, Adriamycin, or double-stranded RNA plus Actinomycin (6, 30). On the other hand, in this study we showed that the peptides containing the MTD of Noxa induce the necrosis (FIG. 2), suggesting that the MTD of Noxa contributes to the necrosis. This view can be further supported by the observation that whereas the membrane blebbings, a key characteristic of apoptosis, in HeLa cells transfected with Noxa 21-40 were observed, the bubble-like structures, a typical cytoplasmic membrane structure of necrosis, in HeLa cells transfected with Noxa 41-54 were observed (data not shown). In addition, the facts that Noxa 41-54-transfected cells in HeLa cells (8) and MTD peptide (FIG. 2B) showed neither cytochrome c release nor caspase-3 activation indicate that the mechanisms for MTD peptide-induced cell death might be similar to that for Noxa MTD-induced cell death.

Questions on the specificity of MTD peptide-induced cell death can be raised by the hydrophobicity of MTD, postulating that it may directly damage the membrane structures by breaking down the lipid bilayer. However, we believe that MTD peptide induces the specific cell death for following reasons. The peptides that cause non-specific membrane damages directly disrupt the membrane structure by itself. However, ΔR8:MTD (FIG. 3D) shows no cell death-inducing activity, indicating that MTD peptide without PTD does not damage the cell membrane. Moreover, the facts that isolated mitochondria showed no morphological changes by MTD peptide, and the mitochondria in Jurkat cells treated with MTD peptide showed the swelled mitochondria (FIG. 2A) indicate that MTD peptide does not simply disrupt the membrane structure itself and may need a cytosolic factor for its cell death-inducing activity. This speculation can be further supported by the facts that mutant MTD peptides including MTDmt3 and MTDmt5 induce no cell death in HeLa cells (FIG. 3A). The differential susceptibilities of different cell lines to MTD peptide are another indication on the specificity of MTD peptide-induced cell death (FIG. 3). Together, these data indicate that MTD peptide does not cause the nonspecific membrane damage or disruption, and MTD peptide needs some cytosolic factor(s) to kill the cells.

REFERENCE

1. Kuwana T, Bouchier-Hayes L, Chipuk J E, et al. BH3 domains of BH3-only proteins differentially regulate Bax-mediated mitochondrial membrane permeabilization both directly and indirectly. Mol Cell 2005; 17: 525-35.
2. Wei M C, Zong W X, Cheng E H, et al. Proapoptotic BAX and BAK: a requisite gateway to mitochondrial dysfunction and death. Science 2001; 292: 727-30.
3. Danial N N, Korsmeyer S J. Cell death: critical control points. Cell 2004; 116: 205-19.
4. Hijikata M, Kato N, Sato T, Kagami Y, Shimotohno K. Molecular cloning and characterization of a cDNA for a novel phorbol-12-myristate-13-acetate-responsive gene that is highly expressed in an adult T-cell leukemia cell line. J Virol 1990; 64: 4632-9.
5. Yu J, Zhang L, Hwang P M, Kinzler K W, Vogelstein B. PUMA induces the rapid apoptosis of colorectal cancer cells. Mol Cell 2001; 7: 673-82.
6. Oda E, Ohki R, Murasawa H, et al. Noxa, a BH3-only member of the Bcl-2 family and candidate mediator of p53-induced apoptosis. Science 2000; 288: 1053-8.
7. Yakovlev A G, Di Giovanni S, Wang G, Liu W, Stoica B, Faden A I. BOK and NOXA are essential mediators of p53-dependent apoptosis. J Biol Chem 2004; 279: 28367-74.
8. Seo Y W, Shin J N, Ko K H, et al. The molecular mechanism of Noxa-induced mitochondrial dysfunction in p53-mediated cell death. J Biol Chem 2003; 278: 48292-9.
9. Ruffolo S C, Shore G C. BCL-2 selectively interacts with the BID-induced open conformer of BAK, inhibiting BAK auto-oligomerization. J Biol Chem 2003; 278: 25039-45.
10. Cheng E H, Wei M C, Weiler S, et al. BCL-2, BCL-X (L) sequester BH3 domain-only molecules preventing BAX- and BAK-mediated mitochondrial apoptosis. Mol Cell 2001; 8: 705-11.
11. Elangovan B, Chinnadurai G. Functional dissection of the pro-apoptotic protein Bik. Heterodimerization with anti-apoptosis proteins is insufficient for induction of cell death. J Biol Chem 1997; 272: 24494-8.
12. Chen L, Willis S N, Wei A, et al. Differential targeting of prosurvival Bcl-2 proteins by their BH3-only ligands allows complementary apoptotic function. Mol Cell 2005; 17: 393-403.
13. Kim H, Rafiuddin-Shah M, Tu H C, et al. Hierarchical regulation of mitochondrion-dependent apoptosis by BCL-2 subfamilies. Nat Cell Biol 2006; 8: 1348-58.
14. Agrawal N, Bettegowda C, Cheong I, et al. Bacteriolytic therapy can generate a potent immune response against experimental tumors. Proc Natl Acad Sci USA 2004; 101: 15172-7.
15. Scaffidi P, Misteli T, Bianchi M E. Release of chromatin protein HMGB1 by necrotic cells triggers inflammation. Nature 2002; 418: 191-5.
16. Wang H, Bloom O, Zhang M, et al. HMG-1 as a late mediator of endotoxin lethality in mice. Science 1999; 285: 248-51.
17. Czabotar P E, Lee E F, van Delft M F, et al. Structural insights into the degradation of Mcl-1 induced by BH3 domains. Proc Natl Acad Sci USA 2007; 104: 6217-22.
18. Day C L, Smits C, Fan F C, Lee E F, Fairlie W D, Hinds M G. Structure of the BH3 domains from the p53-inducible BH3-only proteins Noxa and Puma in complex with Mcl-1. J Mol Biol 2008; 380: 958-71.
19. Szabadkai G, Simoni A M, Bianchi K, et al. Mitochondrial dynamics and Ca2+ signaling. Biochim Biophys Acta 2006; 1763: 442-9.
20. Hajnoczky G, Davies E, Madesh M. Calcium signaling and apoptosis. Biochem Biophys Res Commun 2003; 304: 445-54.
21. Orrenius S, Zhivotovsky B, Nicotera P. Regulation of cell death: the calcium-apoptosis link. Nat Rev Mol Cell Biol 2003; 4: 552-65.
22. Arap W, Haedicke W, Bernasconi M, et al. Targeting the prostate for destruction through a vascular address. Proc Natl Acad Sci USA 2002; 99: 1527-31.
23. Arap W, Pasqualini R, Ruoslahti E. Cancer treatment by targeted drug delivery to tumor vasculature in a mouse model. Science 1998; 279: 377-80.
24. Han S I, Kim Y S, Kim T H. Role of apoptotic and necrotic cell death under physiologic conditions. BMB Rep 2008; 41: 1-10.
25. Schulze-Osthoff K, Krammer P H, Droge W. Divergent signalling via APO-1/Fas and the TNF receptor, two homologous molecules involved in physiological cell death. Embo J 1994; 13: 4587-96.
26. Vercammen D, Brouckaert G, Denecker G, et al. Dual signaling of the Fas receptor: initiation of both apoptotic and necrotic cell death pathways. J Exp Med 1998; 188: 919-30.
27. Lemaire C, Andreau K, Souvannavong V, Adam A. Inhibition of caspase activity induces a switch from apoptosis to necrosis. FEBS Lett 1998; 425: 266-70.
28. Los M, Mozoluk M, Ferrari D, et al. Activation and caspase-mediated inhibition of PARP: a molecular switch between fibroblast necrosis and apoptosis in death receptor signaling. Mol Biol Cell 2002; 13: 978-88.
29. Walisser J A, Thies R L. Poly(ADP-ribose) polymerase inhibition in oxidant-stressed endothelial cells prevents oncosis and permits caspase activation and apoptosis. Exp Cell Res 1999; 251: 401-13.
30. Sun Y, Leaman D W. Involvement of Noxa in cellular apoptotic responses to interferon, double-stranded RNA, and virus infection. J Biol Chem 2005; 280: 15561-8.

What is claimed is:

1. A tumor cell-killing peptide, comprising:
   (a) a mitochondria targeting domain (MTD) at its C-terminal region consisting of an amino acid sequence selected from the group consisting of the amino acid sequences of SEQ ID NOs:1 and 4-7; and
   (b) a tumor homing motif at its N-terminal region, consisting of the amino acid sequence of SEQ ID NO:2 or SEQ ID NO:3; and
   (c) a peptide linker that links the MTD to the tumor homing motif.

2. The tumor cell-killing peptide according to claim 1, wherein the peptide linker is a glycine oligomer.

3. The tumor cell-killing peptide according to claim 1, wherein the peptide linker is a $(Gly)_{2-3}$.

4. The tumor cell-killing peptide according to claim 1, wherein the tumor cell-killing peptide opens a mPT (mitochondrial permeability transition) pore allowing mitochondrial calcium ions to be released into cytosol.

5. The tumor cell-killing peptide according to claim 1, wherein the tumor cell-killing peptide has a killing activity to colon tumor cells, lung tumor cells or cervical tumor cells.

6. The tumor cell-killing peptide according to claim 5, wherein the tumor cell-killing peptide has a killing activity to colon tumor cells.

7. A pharmaceutical composition for treating a cancer, comprising the tumor cell-killing peptide according to claim 1 as an active ingredient.

8. A method for treating a cancer, which comprises administering to a subject in need thereof a composition comprising the tumor cell-killing peptide according to claim 1 as an active ingredient.

* * * * *

SEQUENCE LISTING

```
<160> NUMBER OF SEQ ID NOS: 31

<210> SEQ ID NO 1
<211> LENGTH: 10
<212> TYPE: PRT
<213> ORGANISM: Homo sapiens

<400> SEQUENCE: 1

Lys Leu Leu Asn Leu Ile Ser Lys Leu Phe
1               5                   10
```

```
<210> SEQ ID NO 2
<211> LENGTH: 13
<212> TYPE: PRT
<213> ORGANISM: Artificial Sequence
<220> FEATURE:
<223> OTHER INFORMATION: tumor homing motif derived from Homo sapiens

<400> SEQUENCE: 2

Cys Asn Gly Arg Cys Val Ser Gly Cys Ala Gly Arg Cys
1               5                   10

<210> SEQ ID NO 3
<211> LENGTH: 9
<212> TYPE: PRT
<213> ORGANISM: Artificial Sequence
<220> FEATURE:
<223> OTHER INFORMATION: tumor homing motif derived from Homo sapiens

<400> SEQUENCE: 3

Cys Gly Asn Lys Arg Thr Arg Gly Cys
1               5

<210> SEQ ID NO 4
<211> LENGTH: 10
<212> TYPE: PRT
<213> ORGANISM: Artificial Sequence
<220> FEATURE:
<223> OTHER INFORMATION: MTD2 derived from homo sapiens

<400> SEQUENCE: 4

Lys Ala Leu Asn Leu Ile Ser Lys Leu Phe
1               5                   10

<210> SEQ ID NO 5
<211> LENGTH: 10
<212> TYPE: PRT
<213> ORGANISM: Artificial Sequence
<220> FEATURE:
<223> OTHER INFORMATION: MTD3 derived from homo sapiens

<400> SEQUENCE: 5

Lys Leu Ala Ala Leu Ile Ser Lys Leu Phe
1               5                   10

<210> SEQ ID NO 6
<211> LENGTH: 10
<212> TYPE: PRT
<213> ORGANISM: Artificial Sequence
<220> FEATURE:
<223> OTHER INFORMATION: MTD4 derived from homo sapiens

<400> SEQUENCE: 6

Lys Leu Leu Asn Leu Ile Ala Ala Leu Phe
1               5                   10

<210> SEQ ID NO 7
<211> LENGTH: 10
<212> TYPE: PRT
<213> ORGANISM: Artificial Sequence
<220> FEATURE:
<223> OTHER INFORMATION: MTD5 derived from homo sapiens

<400> SEQUENCE: 7

Lys Ala Leu Asn Leu Ile Ala Ala Leu Phe
1               5                   10
```

<210> SEQ ID NO 8
<211> LENGTH: 24
<212> TYPE: PRT
<213> ORGANISM: Artificial Sequence
<220> FEATURE:
<223> OTHER INFORMATION: PTD and NoxaBH3 fusion peptide derived from
      Homo sapiens

<400> SEQUENCE: 8

Arg Arg Arg Arg Arg Arg Arg Arg Gly Glu Cys Ala Thr Gln Leu Arg
1               5                   10                  15

Arg Phe Gly Asp Lys Leu Asn Phe
            20

<210> SEQ ID NO 9
<211> LENGTH: 36
<212> TYPE: PRT
<213> ORGANISM: Artificial Sequence
<220> FEATURE:
<223> OTHER INFORMATION: PTD and NoxaBH3MTD fusion peptide derived from
      Homo sapiens

<400> SEQUENCE: 9

Arg Arg Arg Arg Arg Arg Arg Arg Gly Glu Cys Ala Thr Gln Leu Arg
1               5                   10                  15

Arg Phe Gly Asp Lys Leu Asn Phe Arg Gln Lys Leu Leu Asn Leu Ile
            20                  25                  30

Ser Lys Leu Phe
        35

<210> SEQ ID NO 10
<211> LENGTH: 21
<212> TYPE: PRT
<213> ORGANISM: Artificial Sequence
<220> FEATURE:
<223> OTHER INFORMATION: PTD and MTD fusion peptide derived from
      Homo sapiens

<400> SEQUENCE: 10

Arg Arg Arg Arg Arg Arg Arg Arg Gly Arg Gln Lys Leu Leu Asn Leu
1               5                   10                  15

Ile Ser Lys Leu Phe
            20

<210> SEQ ID NO 11
<211> LENGTH: 21
<212> TYPE: PRT
<213> ORGANISM: Artificial Sequence
<220> FEATURE:
<223> OTHER INFORMATION: PTD-MTD2 fusion peptide derived from Homo
      sapiens

<400> SEQUENCE: 11

Arg Arg Arg Arg Arg Arg Arg Arg Gly Arg Gly Lys Ala Leu Asn Leu
1               5                   10                  15

Ile Ser Lys Leu Phe
            20

<210> SEQ ID NO 12
<211> LENGTH: 21
<212> TYPE: PRT
<213> ORGANISM: Artificial Sequence
<220> FEATURE:
<223> OTHER INFORMATION: PTD-MTD3 fusion peptide derived from Homo
      sapiens

```
<400> SEQUENCE: 12

Arg Arg Arg Arg Arg Arg Arg Gly Arg Gly Lys Leu Ala Ala Leu
1               5                   10                  15

Ile Ser Lys Leu Phe
            20

<210> SEQ ID NO 13
<211> LENGTH: 21
<212> TYPE: PRT
<213> ORGANISM: Artificial Sequence
<220> FEATURE:
<223> OTHER INFORMATION: PTD-MTD4 fusion peptide derived from Homo
      sapiens

<400> SEQUENCE: 13

Arg Arg Arg Arg Arg Arg Arg Gly Arg Gly Lys Leu Leu Asn Leu
1               5                   10                  15

Ile Ala Ala Leu Phe
            20

<210> SEQ ID NO 14
<211> LENGTH: 21
<212> TYPE: PRT
<213> ORGANISM: Artificial Sequence
<220> FEATURE:
<223> OTHER INFORMATION: PTD-MTD5 fusion peptide derived from Homo
      sapiens

<400> SEQUENCE: 14

Arg Arg Arg Arg Arg Arg Arg Gly Arg Gly Lys Ala Leu Asn Leu
1               5                   10                  15

Ile Ala Ala Leu Phe
            20

<210> SEQ ID NO 15
<211> LENGTH: 21
<212> TYPE: PRT
<213> ORGANISM: Artificial Sequence
<220> FEATURE:
<223> OTHER INFORMATION: PTD-MTDmt1 fusion peptide derived from Homo
      sapiens

<400> SEQUENCE: 15

Arg Arg Arg Arg Arg Arg Arg Gly Arg Gln Ala Ala Leu Asn Leu
1               5                   10                  15

Ile Ser Lys Leu Phe
            20

<210> SEQ ID NO 16
<211> LENGTH: 21
<212> TYPE: PRT
<213> ORGANISM: Artificial Sequence
<220> FEATURE:
<223> OTHER INFORMATION: PTD-MTDmt2 fusion peptide derived from Homo
      sapiens

<400> SEQUENCE: 16

Arg Arg Arg Arg Arg Arg Arg Gly Arg Gln Lys Leu Ala Ala Leu
1               5                   10                  15

Ile Ser Lys Leu Phe
            20

<210> SEQ ID NO 17
```

```
<211> LENGTH: 21
<212> TYPE: PRT
<213> ORGANISM: Artificial Sequence
<220> FEATURE:
<223> OTHER INFORMATION: PTD-MTDmt3 fusion peptide derived from Homo
      sapiens

<400> SEQUENCE: 17

Arg Arg Arg Arg Arg Arg Arg Arg Gly Arg Gln Lys Leu Leu Asn Ala
1               5                   10                  15

Ala Ser Lys Leu Phe
            20

<210> SEQ ID NO 18
<211> LENGTH: 21
<212> TYPE: PRT
<213> ORGANISM: Artificial Sequence
<220> FEATURE:
<223> OTHER INFORMATION: PTD-MTDmt4 fusion peptide derived from Homo
      sapiens

<400> SEQUENCE: 18

Arg Arg Arg Arg Arg Arg Arg Arg Gly Arg Gln Lys Leu Leu Asn Leu
1               5                   10                  15

Ile Ala Ala Leu Phe
            20

<210> SEQ ID NO 19
<211> LENGTH: 21
<212> TYPE: PRT
<213> ORGANISM: Artificial Sequence
<220> FEATURE:
<223> OTHER INFORMATION: PTD-MTDmt5 fusion peptide derived from Homo
      sapiens

<400> SEQUENCE: 19

Arg Arg Arg Arg Arg Arg Arg Arg Gly Arg Gln Lys Leu Leu Asn Leu
1               5                   10                  15

Ile Ser Lys Ala Ala
            20

<210> SEQ ID NO 20
<211> LENGTH: 17
<212> TYPE: PRT
<213> ORGANISM: Artificial Sequence
<220> FEATURE:
<223> OTHER INFORMATION: TU1-MTD fusion peptide derived from Homo
      sapiens

<400> SEQUENCE: 20

Cys Asn Gly Arg Cys Gly Gly Lys Leu Leu Asn Leu Ile Ser Lys Leu
1               5                   10                  15

Phe

<210> SEQ ID NO 21
<211> LENGTH: 25
<212> TYPE: PRT
<213> ORGANISM: Artificial Sequence
<220> FEATURE:
<223> OTHER INFORMATION: TU2-MTD fusion peptide derived from Homo
      sapiens

<400> SEQUENCE: 21

Cys Asn Gly Arg Cys Val Ser Gly Cys Ala Gly Arg Cys Gly Gly Lys
1               5                   10                  15
```

```
Leu Leu Asn Leu Ile Ser Lys Leu Phe
        20                  25

<210> SEQ ID NO 22
<211> LENGTH: 21
<212> TYPE: PRT
<213> ORGANISM: Artificial Sequence
<220> FEATURE:
<223> OTHER INFORMATION: TU3-MTD fusion peptide derived from Homo
      sapiens

<400> SEQUENCE: 22

Cys Gly Asn Lys Arg Thr Arg Gly Cys Gly Gly Lys Leu Leu Asn Leu
1               5                   10                  15

Ile Ser Lys Leu Phe
            20

<210> SEQ ID NO 23
<211> LENGTH: 29
<212> TYPE: DNA
<213> ORGANISM: Artificial Sequence
<220> FEATURE:
<223> OTHER INFORMATION: Noxa 5'-(1)-primer for PCR

<400> SEQUENCE: 23
gaagatctat gcctgggaag aaggcgcgc                                    29

<210> SEQ ID NO 24
<211> LENGTH: 31
<212> TYPE: DNA
<213> ORGANISM: Artificial Sequence
<220> FEATURE:
<223> OTHER INFORMATION: L29A 3'-primer for PCR

<400> SEQUENCE: 24
ctccaaatct cctggcttga gtagcacact c                                 31

<210> SEQ ID NO 25
<211> LENGTH: 31
<212> TYPE: DNA
<213> ORGANISM: Artificial Sequence
<220> FEATURE:
<223> OTHER INFORMATION: L29A 5'-primer for PCR

<400> SEQUENCE: 25
gagtgtgcta ctcaagccag gagatttgga g                                 31

<210> SEQ ID NO 26
<211> LENGTH: 28
<212> TYPE: DNA
<213> ORGANISM: Artificial Sequence
<220> FEATURE:
<223> OTHER INFORMATION: Noxa 3'-(54)-primer for PCR

<400> SEQUENCE: 26
cgaattctca ggttcctgag cagaagag                                     28

<210> SEQ ID NO 27
<211> LENGTH: 33
<212> TYPE: DNA
<213> ORGANISM: Artificial Sequence
<220> FEATURE:
<223> OTHER INFORMATION: L42A 3'-primer for PCR

<400> SEQUENCE: 27
tttggatatc agattcagag ctttctgccg gaa                               33
```

```
<210> SEQ ID NO 28
<211> LENGTH: 31
<212> TYPE: DNA
<213> ORGANISM: Artificial Sequence
<220> FEATURE:
<223> OTHER INFORMATION: L43A 3'-primer for PCR

<400> SEQUENCE: 28
tttggatatc agattcgcaa gtttctgccg g                              31

<210> SEQ ID NO 29
<211> LENGTH: 31
<212> TYPE: DNA
<213> ORGANISM: Artificial Sequence
<220> FEATURE:
<223> OTHER INFORMATION: L45A 3'-primer for PCR

<400> SEQUENCE: 29
tttggatatc gcattcagaa gtttctgccg g                              31

<210> SEQ ID NO 30
<211> LENGTH: 46
<212> TYPE: DNA
<213> ORGANISM: Artificial Sequence
<220> FEATURE:
<223> OTHER INFORMATION: L49A 3'-primer for PCR

<400> SEQUENCE: 30
cgaattctca ggttcctgag cagaaggctt tggatatcag attcag              46

<210> SEQ ID NO 31
<211> LENGTH: 35
<212> TYPE: DNA
<213> ORGANISM: Artificial Sequence
<220> FEATURE:
<223> OTHER INFORMATION: 4mt 3'-primer for PCR

<400> SEQUENCE: 31
gtttggatat cgcattcgca gctttctgcc ggaag                          35
```